US012324916B2

(12) United States Patent
Dinsmoor et al.

(10) Patent No.: US 12,324,916 B2
(45) Date of Patent: Jun. 10, 2025

(54) HYBRID CONTROL POLICY FOR ECAP-SERVOED NEUROMODULATION

(71) Applicant: Medtronic, Inc., Minneapolis, MN (US)

(72) Inventors: David A. Dinsmoor, North Oaks, MN (US); Kristin N. Hageman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 648 days.

(21) Appl. No.: 17/457,189

(22) Filed: Dec. 1, 2021

(65) Prior Publication Data

US 2022/0218996 A1   Jul. 14, 2022

Related U.S. Application Data

(60) Provisional application No. 63/136,942, filed on Jan. 13, 2021.

(51) Int. Cl.
| | |
|---|---|
| *A61N 1/00* | (2006.01) |
| *A61N 1/05* | (2006.01) |
| *A61N 1/36* | (2006.01) |
| *A61N 1/372* | (2006.01) |

(52) U.S. Cl.
CPC .......... *A61N 1/36132* (2013.01); *A61N 1/05* (2013.01); *A61N 1/3601* (2013.01); *A61N 1/36062* (2017.08); *A61N 1/36114* (2013.01); *A61N 1/36135* (2013.01); *A61N 1/36192* (2013.01);

(Continued)

(58) Field of Classification Search
USPC .......................................................... 607/2
See application file for complete search history.

(56) References Cited

U.S. PATENT DOCUMENTS

| | | | |
|---|---|---|---|
| 10,183,168 B2 | 1/2019 | Baru et al. | |
| 2015/0323912 A1* | 11/2015 | Shamsuzzoha | G05B 11/42 700/37 |
| 2017/0361101 A1* | 12/2017 | Single | A61N 1/36062 |

(Continued)

OTHER PUBLICATIONS

International Preliminary Report on Patentability from International Application No. PCT/US2021/061636 dated Jul. 27, 2023, 8 pp.

(Continued)

*Primary Examiner* — Aaron F Roane
(74) *Attorney, Agent, or Firm* — Shumaker & Sieffert, P.A.

(57) ABSTRACT

Systems, devices, and techniques for adjusting electrical stimulation are described. For example, processing circuitry is configured to receive, via a sensing electrode located at a target region of a patient, a plurality of evoked compound action potential (ECAP) signals elicited from respective electrical stimuli delivered to the patient; determine, based on the plurality of ECAP signals, an aggressor category for at least some ECAP signals of the plurality of ECAP signals, the aggressor category determined from a plurality of aggressor categories; determine, based on the aggressor category, a set of control policy parameters that at least partially define closed-loop control of stimulation therapy; and controlling delivery of the stimulation therapy according to at least the set of control policy parameters and one or more subsequent ECAP signals.

23 Claims, 8 Drawing Sheets

(52) U.S. Cl.
CPC ..... *A61N 1/36196* (2013.01); *A61N 1/37235* (2013.01)

(56) References Cited

U.S. PATENT DOCUMENTS

| | | | |
|---|---|---|---|
| 2018/0333582 A1* | 11/2018 | Grill | A61B 5/4064 |
| 2019/0201694 A1 | 7/2019 | Hsu et al. | |
| 2020/0038660 A1* | 2/2020 | Torgerson | A61N 1/36164 |
| 2021/0008373 A1 | 1/2021 | Single et al. | |
| 2021/0187297 A1 | 6/2021 | Pulliam et al. | |

OTHER PUBLICATIONS

International Search Report and Written Opinion of International Application No. PCT/US2021/061636, dated Mar. 22, 2022, 11 pp.

* cited by examiner

HYBRID CONTROL POLICY FOR ECAP-SERVOED NEUROMODULATION

This application claims priority from U.S. Provisional Patent Application No. 63/136,942, filed on Jan. 13, 2021, the entire contents of which are incorporated herein by reference.

TECHNICAL FIELD

This disclosure generally relates to electrical stimulation, and more specifically, control of electrical stimulation.

BACKGROUND

Medical devices may be external or implanted and may be used to deliver electrical stimulation to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered by the medical device as a train of pulses, and the values of the parameters defining the pulses may be altered.

SUMMARY

In general, systems, devices, and techniques are described for managing the delivery of electrical stimulation based on evoked compound action potential (ECAP) signals sensed from a patient. Any of a number of potential movement-based factors, referred to herein as "aggressors," may vary the distance between implanted electrodes and target nerves. For instance, "transient" aggressors may include a generally non-repetitive motion of or by the patient, such as a change in posture or the like, that unintentionally modifies the distance between the electrodes and the target nerves. For example, electrodes implanted along the spinal column are closer to the spinal cord when a subject lies in a supine posture state as compared to a standing posture state. Similarly, the implanted electrodes may move closer to the spinal cord when a subject coughs or sneezes.

As another example, "cyclic" or "cyclical" aggressors may include any periodic or repetitive motion of or within the patient, such as the patient's heartbeat, respiration, or digestive cycle, that unintentionally modifies the distance between the electrodes and the target nerves. This changing distance between the electrodes and target tissue affects neural recruitment for a given intensity of delivered stimulation and can cause the patient's perception and/or therapeutic benefit to also change. Therefore, a characteristic value of the ECAP signal can represent the change in distance, and a system can modulate electrical stimulation using the characteristic value as feedback.

As a result of these one or more aggressors, the different distances between the electrodes and target tissue may cause the patient to have different levels of sensitivity to electrical stimulation. In this manner, an amplitude of the detected ECAP signal can depend at least in part on these aggressors. Since different types of aggressors can change the rate or frequency with which the distance between electrodes and nerves changes, a system may benefit from different rates of change or performance characteristics when adjusting stimulation based on sensed ECAP values. As described herein, a system may determine a type (e.g., observed, identified, or detected) of aggressor, or in some examples, a category encompassing similar types of potential aggressors, and use that type of aggressor to inform how the system uses the ECAP signal in a control policy that defines changes to stimulation parameter values for subsequent stimulation pulses, such as a frequency, an amplitude, a pulse width, and/or a pulse shape.

Generally, informed stimulation pulses may be configured to contribute to a therapeutic effect of the patient, but ECAP signals may not be detectable from these informed stimulation pulses. Therefore, control stimulation pulses having a pulse width shorter, or a frequency slower, than the informed stimulation pulses may be delivered to the patient in order to detect elicited ECAP signals. The control stimulation pulses may or may not contribute to a therapeutic effect for the patient. In one example, the system may select a gain value associated with a determined aggressor or aggressor category for adjusting parameter values for one or both of the control stimulation pulses and the informed stimulation pulses. The gain value may be associated with the rate of change in ECAP values (or associated gain values) for that determined aggressor or aggressor category. In addition, or alternatively, the system may select a target ECAP characteristic value according to the determined aggressor or aggressor category.

In one example, a system includes processing circuitry configured to receive, from a sensing electrode located at a target region of a patient, a plurality of evoked compound action potential (ECAP) signals elicited from respective electrical stimuli delivered to the patient; determine, based on the plurality of ECAP signals, an aggressor category for at least some ECAP signals of the plurality of ECAP signals, the aggressor category determined from a plurality of aggressor categories; determine, based on the aggressor category, a set of control policy parameters that at least partially define closed-loop control of stimulation therapy; and control delivery of the stimulation therapy according to at least the set of control policy parameters and one or more subsequent ECAP signals.

In another example, a method includes receiving, via a sensing electrode located at a target region of a patient, a plurality of evoked compound action potential (ECAP) signals elicited from respective electrical stimuli delivered to the patient; determining, based on the plurality of ECAP signals, an aggressor category for at least some ECAP signals of the plurality of ECAP signals, the aggressor category determined from a plurality of aggressor categories; determining, based on the aggressor category, a set of control policy parameters that at least partially define closed-loop control of stimulation therapy; and controlling delivery of the stimulation therapy according to at least the set of control policy parameters and one or more subsequent ECAP signals.

In another example, a computer-readable storage medium includes instructions that, when executed by processing circuitry, cause the processing circuitry to receive, from a sensing electrode located at a target region of a patient, a plurality of evoked compound action potential (ECAP) signals elicited from respective electrical stimuli delivered to the patient; determine, based on the plurality of ECAP signals, an aggressor category for at least some ECAP signals of the plurality of ECAP signals, the aggressor category determined from a plurality of aggressor categories; determine, based on the aggressor category, a set of control policy parameters that at least partially define closed-loop control of stimulation therapy; and control delivery of the stimulation therapy according to at least the set of control policy parameters and one or more subsequent ECAP signals.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages of the techniques will be apparent from the description and drawings, and from the claims.

BRIEF DESCRIPTION OF DRAWINGS

Like reference characters denote like elements throughout the description and figures.

DETAILED DESCRIPTION

Figure 1:
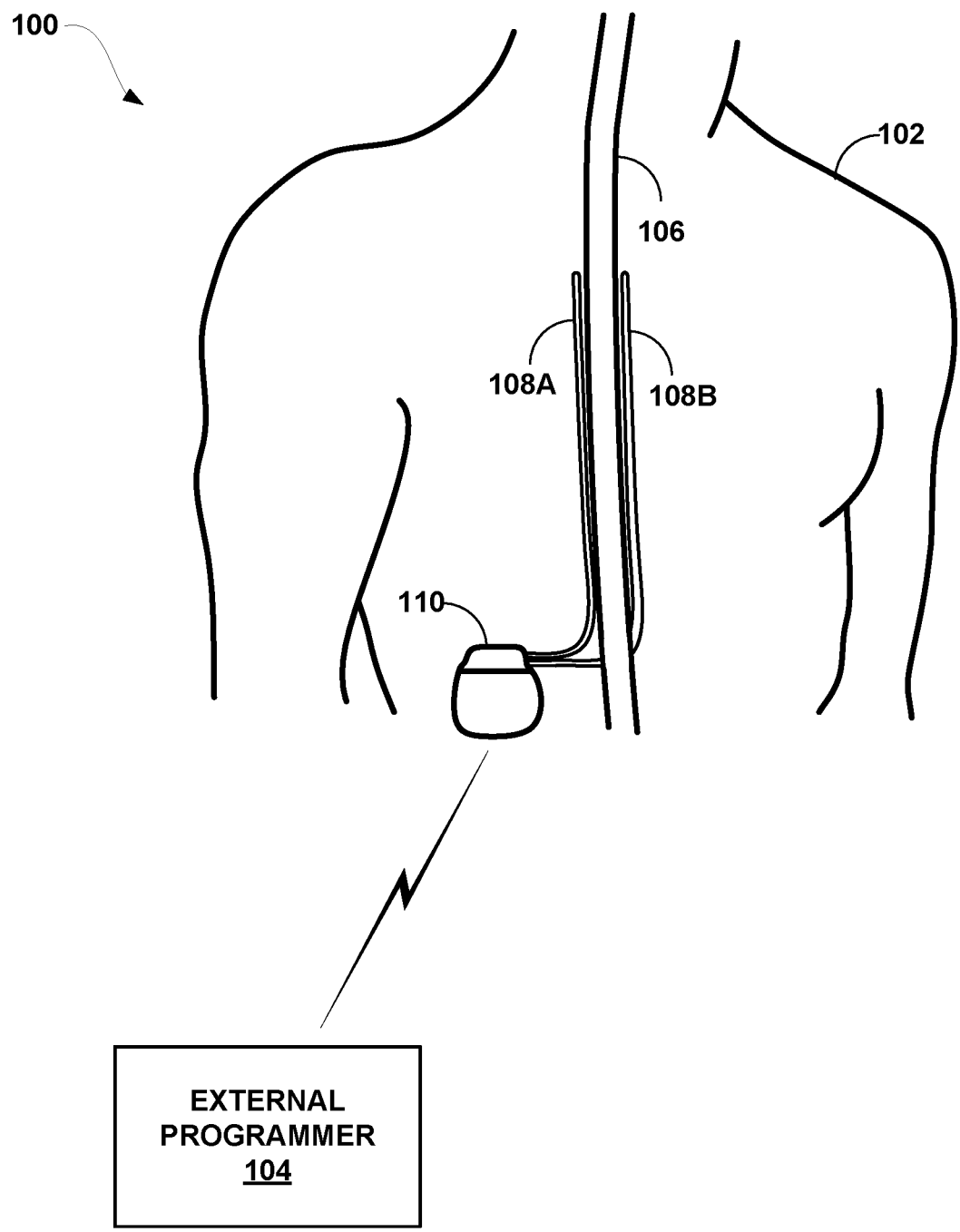
FIG. 1 is a conceptual diagram illustrating an example system that includes a medical device programmer and an IMD according to the techniques of the disclosure.

The disclosure describes examples of medical devices, systems, and techniques for adjusting electrical stimulation delivered to a patient based on a determined (e.g., observed, detected, or identified) type of movement-based factor (e.g., a type of aggressor) of the patient and one or more characteristics of ECAP signals. Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous-system disorders, muscle disorders, etc. However, as the patient moves, the distance between the electrodes and the target tissues changes. Since neural recruitment at the nerves is a function of stimulation intensity (e.g., amplitude and/or pulse frequency) and distance between the target tissue and the electrodes, movement of the electrode closer to the target tissue may result in increased neural recruitment (e.g., possibly associated with painful sensations or adverse motor function), and movement of the electrode farther from the target tissue may result in decreased efficacy of the therapy for the patient. Certain patient movements, referred to herein as "aggressors," (which may or may not include patient activity) may be representative of respective distances (or changes in distance) between electrodes and nerves and thus be an informative feedback variable for modulating stimulation therapy. For instance, "transient" aggressors may include virtually any non-repetitive motion of or by the patient, such as a change in posture or the like, that unintentionally modifies the distance between the electrodes and the target nerves.

In some such examples, a patient may experience discomfort or pain caused by transient aggressors, which is referred to herein as "transient overstimulation." The electrodes can move closer to the target tissue due to a number of transient aggressors including, but not limited to, coughing, sneezing, laughing, Valsalva maneuvers, leg lifting, cervical motions, deep breathing, or another transient patient movement. If a system is delivering stimulation during these movements, the patient may perceive the stimulation as stronger (and possibly uncomfortable) due to the decreased distance between electrodes and target tissue in a short amount of time. Although a patient may anticipate such movements and preemptively reduce stimulation intensity in an attempt to avoid these uncomfortable sensations, these patient actions interfere with normal activities and may not be sufficient to avoid uncomfortable stimulation at all times.

As another example, "cyclic" or "cyclical" aggressors may include virtually any periodic or repetitive motion of the patient, such as the patient's heartbeat, respiration, or digestive cycle, that unintentionally modifies the distance between the electrodes and the target nerves. With cyclic aggressors, as compared to with transient aggressors, the electrodes may move both toward the target tissue and away from the target tissue in an alternating fashion according to a substantially predictable pattern that may be observed across a plurality of sensed ECAP signals. In some examples, but not all examples, cyclic aggressors may have a relatively lower or reduced effect on the sensed ECAP signals compared to many transient aggressors, such as when the cyclic aggressor includes a substantially subtle, physiological motion such as respiration or the cardiac cycle.

It should be noted that the aggressor categories of "transient" aggressors and "cyclic" aggressors, as described herein, are merely two examples of potential categories for grouping different aggressors (e.g., different sources of movement) according to common, easily observable aggressor characteristics. However, as there are virtually any number of potential aggressor sources, there are likewise any number of aggressor categories into which different aggressors may be grouped for the purposes of applying the techniques of this disclosure.

ECAPs are a measure of neural recruitment because each ECAP signal represents the superposition of electrical potentials generated from a population of axons firing in response to an electrical stimulus (e.g., a stimulation pulse). Changes in a characteristic of an ECAP signal (e.g., an amplitude of a portion of the signal or the area-under-the-curve of the signal) occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude, or area-under-the-curve, or a rate of change thereof across a plurality of consecutive ECAP signals). Therefore, a system can determine that the distance between electrodes and nerves has increased or decreased in response to determining that the measured ECAP characteristic value has increased or decreased. For example, if the set of parameter values stays the same and the ECAP characteristic value of amplitude increases, the system can determine that the distance between electrodes and the nerve has decreased.

In some examples, effective stimulation therapy may rely on a certain level of neural recruitment at a target nerve. This effective stimulation therapy may provide relief from one or more conditions (e.g., patient-perceived pain) without an unacceptable level of side effects (e.g., overwhelming perception of stimulation). However, due to one or more aggressors (e.g., if the patient changes posture, cardiac cycle, respiration cycle, or otherwise engages in physical activity), the distance between the electrodes and the nerve can change as well. This change in distance can cause loss of effective therapy and/or side effects if the parameter values that define stimulation are not adjusted to compensate for the change in distance. Moreover, the different distance between electrodes and the target nerve (e.g., caused by a shift from one posture state to another, or another type of aggressor) may also result in different sensitivities to stimulation intensity (e.g., smaller distances may result in greater sensitivities to changes in stimulation intensity). If a system does not adjust the control policy for these changes in a patient, adjustments to stimulation parameter values may not be sufficient to maintain effective therapy or may provide stimulation that is too strong for a particular posture or during/after an aggressor. Therefore, it may be beneficial to maintain effective therapy by the system adjusting how stimulation intensity is changed in response to the presence of an aggressor and/or changing target ECAP characteristic values when an aggressor factor is determined (e.g., detected, observed, or identified).

As described herein, systems, devices, and techniques provide solutions to one or more of the above-referenced problems by adjusting electrical stimulation therapy delivered to a patient based on a determined category of aggressor and one or more characteristics of ECAP signals. As discussed above, when a patient moves (in some form or another), the distance between implanted electrodes and target nerves changes. For example, electrodes implanted along the spinal column move to a position closer to the spinal cord when a subject moves between a supine posture state and a standing posture state. Since this movement state can affect the distance between the electrodes and target nerve, the system may detect or otherwise determine the effects of this transient aggressor and adjust one or more aspects of the control policy employed by the system to modulate stimulation therapy in response to detected ECAP signals. In some examples, the system may select a therapy program or set of stimulation parameter values according to the detected aggressor (or aggressor category) of the patient.

The system may store or otherwise obtain gain values, target ECAP characteristic values, or other factors that affect modulation of stimulation associated with respective aggressors or aggressor categories. Electrical stimulation may be delivered to a patient by the medical device in a train of stimulation pulses, and parameters that define the stimulation pulses may include pulse amplitude (current and/or voltage), pulse frequency, pulse width, pulse shape, and/or electrode combination. The system may alter, adjust, change, or otherwise modulate one or more parameters of the stimulation pulses over time in order to maintain a desired level of stimulation efficacy and/or comfort for the patient. For example, the system may utilize different gain values for different types of aggressors in order to appropriately respond to changes in ECAP values (e.g., increase or decrease stimulation amplitude at a rate appropriate for the type of aggressor).

Nerve impulses detectable as the ECAP signal travel quickly along the nerve fiber after the delivered stimulation pulse first depolarizes the nerve. If the stimulation pulse that elicits the ECAP signal is delivered by first electrodes has a pulse width that is too long, different electrodes configured to sense the ECAP will sense the stimulation pulse itself as an artifact that obscures the lower amplitude ECAP signal. Although sensing electrodes could be positioned farther away from where the stimulation pulse is delivered to avoid this artifact, the ECAP signal loses fidelity as the electrical potentials propagate from the electrical stimulus because different nerve fibers propagate electrical potentials at different speeds. Therefore, sensing the ECAP at a farther distance from the stimulating electrodes may avoid the artifact caused by a stimulation pulse with a long pulse width, but the ECAP signal may lose fidelity needed to detect changes to the ECAP signal that occur when the electrode-to-target-tissue distance changes. In other words, the system may not be able to identify, at any distance from the stimulation electrodes, ECAPs elicited by certain stimulation pulses having relatively long pulse widths that interfere with detection of ECAP signals (e.g., stimulation pulses that may be configured to provide a therapeutic effect for the patient).

To avoid this ECAP detection problem with some stimulation pulses, a medical device may be configured to deliver a plurality of control pulses and a plurality of informed pulses in some examples. Informed pulses may be configured to contribute to a therapeutic effect for the patient, but the informed pulses may have a stimulation parameter, such as a pulse width or a high stimulation frequency, that overlaps with the ECAP signal and prevents the system from detecting the ECAP signal or otherwise using the ECAP signal for feedback for modulating parameter values of the informed pulses. The plurality of control pulses, on the other hand, may be configured to elicit detectable ECAP signals. For example, the control pulses may have a pulse width that is short enough to avoid interfering with the ECAP signal detection. The control pulses may or may not contribute to a therapeutic effect for the patient. In this manner, the system may be configured to adjust one or more parameters that define the informed pulses based on the detectable ECAP signals elicited by one or more control pulses.

In one example described herein, a medical device can deliver a plurality of informed pulses to provide a therapy to the patient and a plurality of control pulses. At least some of the control pulses may elicit a detectable ECAP signal without the primary purpose of providing a therapy to the patient. The control pulses may be interleaved with the delivery of the informed pulses. For example, the medical device may alternate the delivery of informed pulses with control pulses such that a control pulse is delivered, and an ECAP signal is sensed, between consecutive informed pulses. In some examples, multiple control pulses are delivered, and respective ECAP signals sensed, between the delivery of consecutive informed pulses. In some examples, multiple informed pulses will be delivered between consecutive control pulses. In any case, the informed pulses may be delivered according to a predetermined pulse frequency selected so that the informed pulses can produce a therapeutic result for the patient. One or more control pulses are then delivered, and the respective ECAP signals sensed, within one or more time windows between consecutive informed pulses delivered according to the predetermined pulse frequency. In this manner, a medical device can administer informed pulses from the medical device uninterrupted while ECAPs are sensed from control pulses delivered during times at which the informed pulses are not being delivered. In other examples described herein, ECAPs are sensed by the medical device in response to the informed pulses delivered by the medical device, and control pulses are not used to elicit ECAPs.

The system may monitor one or more characteristic values that represent detected ECAP signals and adjust a stimulation parameter value in an attempt to achieve a target ECAP characteristic value. The system may adjust an informed parameter that at least partially defines subsequent informed pulses and may adjust a control parameter that at least partially defines subsequent control pulses. When adjusting the informed parameter value and/or the control parameter value in response to determining that the sensed characteristic value of the ECAP signal is below or above the target ECAP characteristic value, the system may employ a gain value that represents the magnitude, or rate, of change applied to a stimulation parameter in order to achieve the target ECAP characteristic value. The gain value may be the same or different for informed pulses and control pulses. As described herein, the system may select the gain value based on the type of aggressor detected for the patient and/or that affects the patient. In some examples, the system may apply a scaling factor or otherwise adjust the gain value so that it is appropriate for informed pulses and control pulses that may have different amplitudes or other parameters. For example, if the control pulse has a higher amplitude value than the informed pulse, the system may effectively reduce the gain value, or reduce the effect of the gain value, on the change to the informed pulse amplitude because the lower amplitude value of the informed pulse may not need to be changes as much as the control pulse amplitude. The system can thus increase or decrease a stimulation parameter according to the gain value in order to maintain the target ECAP characteristic value.

In some examples, the gain value may be a multiplier applied to a difference between a target ECAP characteristic value and a detected ECAP characteristic value. If the gain value is constant, the result is a stimulation parameter value that changes linearly. For example, the system may select one gain value for any detected ECAP characteristic value that is less than the target ECAP characteristic value, and the system may select a different gain value for any detected ECAP characteristic value that is greater than the target ECAP characteristic value. In other examples, the gain value may be calculated using a function that may be linear or non-linear. Put another way, for a given input or set of inputs (e.g., the detected ECAP characteristic value and/or posture state may be an input that affects the calculated gain value) the system may calculate different gain values for increasing stimulation intensity and/or decreasing stimulation intensity.

In one example, the system may determine a gain value that changes for different aggressors, for different aggressor categories, for different sensed ECAP characteristic values, or for different differences between the sensed ECAP characteristic value and a target ECAP characteristic value. A changing gain value (via a linear or non-linear function) would result in a non-linear function that determines the adjusted stimulation parameter (e.g., the output of the non-linear function). For example, the system may adjust the stimulation parameter value exponentially or logarithmically according to the difference between the sensed ECAP characteristic value and the threshold ECAP amplitude. In one example, the gain value is calculated by multiplying the difference between the sensed ECAP characteristic value and the threshold ECAP amplitude to a multiplier (e.g., a linear function) such that the gain value changes according to that difference between the sensed ECAP characteristic value and the threshold ECAP amplitude. In some examples, the gain value may represent a value selected from a table that stores gain values for respective aggressors, aggressor categories, and/or difference values between the sensed ECAP characteristic value and the threshold ECAP amplitude. The table may result in a linear or non-linear function for determining the next stimulation parameter value.

For example, a larger gain value will cause the system to make a larger adjustment to a stimulation parameter (e.g., informed parameter or control parameter) for the same stimulation pulse than the adjustment resulting from a smaller gain value. For a non-linear function, this comparison in gain value can be made relative to the same value for the difference between the sensed ECAP characteristic value and the threshold ECAP amplitude (e.g., the value difference representing an input value to the gain function). Thus, for a given input value of the gain function (or set of input values) the corresponding gain value (or set of gain values) is changed. For ease of discussion, various examples discuss the change in gain value relative to a linear function. It is understood that a non-linear function may also be used in such embodiments, where the relative change in gain value is thereby relative to the same value for the difference between the sensed ECAP characteristic value and the threshold ECAP amplitude.

Without different gain values for different aggressors or aggressor categories, a system may respond too slowly or too quickly with adjustments to stimulation parameter values. If the gain value is too large for the aggressor or aggressor category, the system may overcorrect a stimulation parameter value (e.g., cause an uncomfortable sensation or reduce therapy efficacy). If the gain value is too small for the aggressor or aggressor category, the system may require many iterations of adjustments to the stimulation parameter before the appropriate stimulation intensity is provided (e.g., also causing a prolonged uncomfortable sensation or a prolonged period of ineffective therapy). Generally, aggressors associated with farther distances between the electrodes and target nerve may generally have larger gain values than aggressors associated with closer distances between the electrodes and target nerve. In this manner, smaller gain values may be associated with smaller distances between electrodes and the target nerve (e.g., aggressors more sensitive to changes in stimulation intensity). Conversely, larger gain values may be associated with larger distances between electrodes and the target nerve (e.g., aggressors less sensitive to changes in stimulation intensity). In another respect, aggressors associated with a greater change in distance between the electrodes and target nerve (regardless of whether the change is toward or away from the target nerve), corresponding to a relatively larger variability in sensed ECAP values, may generally have larger gain values than aggressors associated with a smaller change in distance between the electrodes and target nerve, corresponding to a relatively smaller variability in sensed ECAP values. In some examples, but not all examples, aggressors of the "transient" category may be more likely to have larger gain values than aggressors of the "cyclic" category, which may often cause relatively minor variation in sensed ECAP values.

In some examples, the target ECAP characteristic value may be the same for some or all aggressors or all aggressors within a common aggressor category, but the target ECAP characteristic value may be different between aggressors or aggressor categories in other examples. In this manner, the system may select the target ECAP characteristic value associated with the detected aggressor or aggressor category.

In another type of control policy (e.g., another type of closed-loop feedback scheme), the system may employ a threshold ECAP characteristic value instead of a target ECAP characteristic value. The system may monitor characteristic values for sensed ECAP signals and reduce one or more stimulation parameter values (e.g., informed parameter values and/or control parameter values) from a predetermined value only in response to the characteristic value exceeding the threshold ECAP characteristic value. In other words, the system may be configured to attempt to keep characteristic values of sensed ECAP signals below the threshold ECAP characteristic value and only increase the stimulation parameter back up to the predetermined value in response to the characteristic value dropping back below the threshold ECAP characteristic value. In some examples, the system may select the gain value used for adjusting the stimulation parameter according to a determined aggressor or aggressor category. In addition, or alternatively, the system may select the threshold ECAP characteristic value according to a determined aggressor category of the patient.

In some examples, stimulation parameter values may be predetermined and/or automatically adjusted by the system based on characteristic values of ECAP signals, determined aggressor(s), and other types of feedback. An external programmer for an IMD may provide a variety of features to support association of stimulation parameter values and/or characteristic values of ECAP signals with different aggressors or aggressor categories. As one example, the programmer may receive user input indicating a common aggressor or aggressor category and the ECAP signals and/or corresponding characteristic values to be associated with that aggressor or aggressor category. As another example, a patient may indicate a value for a previously undefined stimulation parameter value for a particular aggressor or aggressor category. The indicated value may be defined for the aggressor or aggressor category. As another example, a user may link multiple aggressors into a common aggressor category and select a set of stimulation parameter values for delivery of therapy for each of the aggressors within the common category. In this manner, it may not be necessary to specify separate sets of stimulation parameter values for each individual type of aggressor.

In some examples, a medical device, e.g., an implantable medical device (IMD), that delivers electrical stimulation may identify the presence of one or more aggressors, based on a characteristic or "signature" across a plurality of consecutive ECAP signals (e.g., based on a sudden change between ECAP signals, or based on a shape or pattern of the ECAP signals over time). Additionally or alternatively, the IMD may also employ an aggressor detector (e.g., one or more sensors) that detects the presence of one or more aggressors. In other examples, the IMD may receive data from one or more separate devices that sense the presence of one or more aggressors affecting the sensed ECAP signals. The IMD may then adjust one or more stimulation parameters in response to different aggressors or aggressor categories (e.g., an aggressor that is currently dominating a variability within sensed ECAP signals), e.g., as indicated by the aggressor detector.

A user may define stimulation parameter values (e.g., informed parameter values for informed pulses and/or control parameter values for control pulses) for delivery of therapy to a patient and associate the stimulation parameter values with multiple types of aggressors based on user input, e.g., simultaneously. As another example, upon storing a set of pre-established aggressor definitions for delivery of aggressor-responsive therapy, a device may permit a patient to submit a request (e.g., via a patient programmer) to update the set of pre-established aggressor definitions. For example, the patient programmer may be configured to receive user input changing the definitions of one or more aggressors or aggressor categories. In addition, an aggressor definition may be modified based on user-therapy adjustments and/or aggressor information. In some cases, the aggressor or aggressor category may be expanded and split. In other cases, the aggressor or aggressor category may be reduced in size based on aggressor information. Hence, using one or more of the features described in this disclosure, stimulation parameter values may be flexibly, conveniently, and efficiently specified for various aggressors or aggressor categories, including predetermined aggressors and patient-created aggressors.

Informed pulses and control pulses are generally described herein as different stimulation pulses reflective of different types of electrical stimulation. However, the different types of electrical stimulation, and their respective pulses, may be described with different attributes. For example, a first type of electrical stimulation may include first pulses (such as informed pulses) configured to primarily contribute to a therapy for a patient. The first pulses of this first type of electrical stimulation may also have one or more characteristics (e.g., a pulse width) that prevent or reduce the ability of the system to detect ECAP signals elicited from the first pulses of the first type of electrical stimulation because an artifact representative of the first pulses themselves overlaps with and obscures at least a portion of the respective elicited ECAP signal. A second type of electrical stimulation may include second pulses (such as control pulses) defined by one or more parameter values selected to elicit ECAP signals that are sensed and detectable by the system. The second pulses may thus be referred to as "sense pulses" or "test pulses" since the second pulses are configured to elicit a detectable ECAP signal. For example, the second pulses of the second type of electrical stimulation may improve the detectability of the ECAP signal such as not to generate an artifact that obscures the ECAP signals or otherwise prevents or reduces the ability of the system to detect the ECAP signal from each of the second pulses. In addition, the second pulses may be defined by parameter values selected to elicit an ECAP signal that is used to at least modify one or more parameter values of the first pulses of the first type of electrical stimulation. The first pulses may thus differ from the second pulses by at least one parameter (e.g., current and/or voltage amplitude, pulse width, and/or frequency). The first pulses may be at least partially interleaved with at least some of the second pulses. For example, the system may alternate delivery of one first pulse with delivery of one second pulse. In another example, the number of first pulses may differ from the number of second pulses by a ratio or percentage. The ratio could be 1:1 when the first and second pulses are fully interleaved. The ratio could be 10:1 first pulses to second pulses in examples in which the second pulses are delivered less frequently than the first pulses. In other examples, the ratio could be 1:4 of first pulses to second pulses when the second pulses (and respective sensed ECAP signals) occur more frequently than the first pulses. The second pulses may or may not contribute to a therapy and/or sensation perceived by the patient, but the primary purpose of the second pulses is to elicit respective ECAP signals that are detectable by the system separate from any sensed artifacts representative of the second pulses themselves.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system 100 that includes implantable medical device (IMD) 110 to deliver electrical stimulation therapy to patient 102. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 108A and 108B, and external programmer 104 shown in conjunction with a patient 102, who is ordinarily a human patient. In the example of FIG. 1, IMD 110 is an implantable electrical stimulator that is configured to generate and deliver electrical stimulation therapy to patient 102 via one or more electrodes of electrodes of leads 108A and/or 108B (collectively, "leads 108"), e.g., for relief of chronic pain or other symptoms. In other examples, IMD 110 may be coupled to a single lead carrying multiple electrodes or more than two leads each carrying multiple electrodes. In some examples, the stimulation signals, or pulses (e.g., control pulses), may be configured to elicit detectable ECAP signals that IMD 110 may use to identify one or more aggressors and/or determine how to adjust one or more parameters that define stimulation therapy. IMD 110 may be a chronic electrical stimulator that remains implanted within patient 102 for weeks, months, or even years. In other examples, IMD 110 may be a temporary, or trial, stimulator used to screen or evaluate the efficacy of electrical stimulation for chronic therapy. In one example, IMD 110 is implanted within patient 102, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 102. In this example, IMD 110 may be constructed with a biocompatible housing, such as titanium or stainless steel, or a polymeric material such as silicone, polyurethane, or a liquid crystal polymer, and surgically implanted at a site in patient 102 near the pelvis, abdomen, or buttocks. In other examples, IMD 110 may be implanted within other suitable sites within patient 102, which may depend, for example, on the target site within patient 102 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 102 via one or more electrodes (not shown) of implantable leads 108. In the example of FIG. 1, leads 108 carry electrodes that are placed adjacent to the target tissue of spinal cord 106. One or more of the electrodes may be disposed at a distal tip of a lead 108 and/or at other positions at intermediate points along the lead. Leads 108 may be implanted and coupled to IMD 110. The electrodes may transfer electrical stimulation generated by an electrical stimulation generator in IMD 110 to tissue of patient 102. Although leads 108 may each be a single lead, lead 108 may include a lead extension or other segments that may aid in implantation or positioning of lead 108. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 108 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 108 will be described for purposes of illustration.

The deployment of electrodes via leads 108 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 108 are linear leads having eight ring electrodes along the axial length of the lead. In another example, the electrodes are segmented rings arranged in a linear fashion along the axial length of the lead and at the periphery of the lead.

The stimulation parameter set of a stimulation program that defines the stimulation pulses of electrical stimulation therapy by IMD 110 through the electrodes of leads 108 may include information identifying which electrodes have been selected for delivery of stimulation according to a stimulation program, the polarities of the selected electrodes, i.e., the electrode combination for the program, voltage or current amplitude, pulse frequency, pulse width, or pulse shape of stimulation delivered by the electrodes. These stimulation parameters values that make up the stimulation parameter set that defines pulses may be predetermined parameter values defined by a user and/or automatically determined by system 100 based on one or more factors or user input. Informed pulses may be defined by a set of informed stimulation parameter values and control pulses may be defined by a set of control stimulation parameter values.

Although FIG. 1 is directed to SCS therapy, e.g., used to treat pain, in other examples system 100 may be configured to treat any other condition that may benefit from electrical stimulation therapy. For example, system 100 may be used to treat tremors, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 102.

In some examples, lead 108 includes one or more sensors configured to allow IMD 110 to monitor one or more parameters of patient 102, such as patient activity, pressure, temperature, or other characteristics. The one or more sensors may be provided in addition to, or in place of, therapy delivery by lead 108.

IMD 110 is generally configured to deliver electrical stimulation therapy (e.g., informed pulses and/or control pulses) to patient 102 via selected combinations of electrodes carried by one or both of leads 108, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated in FIG. 1, the target tissue is tissue proximate spinal cord 106, such as within an intrathecal space or epidural space of spinal cord 106, or, in some examples, adjacent nerves that branch off spinal cord 106. Leads 108 may be introduced into spinal cord 106 in via any suitable region, such as the thoracic, cervical or lumbar regions. Stimulation of spinal cord 106 may, for example, prevent pain signals from traveling through spinal cord 106 and to the brain of patient 102. Patient 102 may perceive the interruption of pain signals as a reduction in pain and, therefore, efficacious therapy results. In other examples, stimulation of spinal cord 106 may produce paresthesia which may be reduce the perception of pain by patient 102, and thus, provide efficacious therapy results.

IMD 110 is configured to generate and deliver electrical stimulation therapy to a target stimulation site within patient 102 via the electrodes of leads 108 to patient 102 according to one or more therapy stimulation programs. A therapy stimulation program may generally define informed pulses, but may also define control pulses (e.g., if the control pulses also contribute to a therapeutic effect). A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc., for stimulation pulses delivered by IMD 110 according to that program.

A user, such as a clinician or patient 102, may interact with a user interface of an external programmer 104 to program IMD 110. Programming of IMD 110 may refer generally to the generation and transfer of commands, programs, or other information to control the operation of IMD 110. In this manner, IMD 110 may receive the transferred commands and programs from external programmer 104 to control stimulation, such as stimulation pulses that provide electrical stimulation therapy. For example, external programmer 104 may transmit therapy stimulation programs, stimulation parameter adjustments, therapy stimulation program selections, posture states, user input, or other information to control the operation of IMD 110, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 102 and, in many cases, may be a portable device that may accompany patient 102 throughout the patient's daily routine. For example, a patient programmer may receive input from patient 102 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 104 may include, or be part of, an external charging device that recharges a power source of IMD 110. In this manner, a user may program and charge IMD 110 using one device, or multiple devices.

As described herein, information may be transmitted between external programmer 104 and IMD 110. Therefore, IMD 110 and external programmer 104 may communicate via wireless communication using any techniques known in the art. Examples of communication techniques may include, for example, radiofrequency (RF) telemetry and inductive coupling, but other techniques are also contemplated. In some examples, external programmer 104 includes a communication head that may be placed proximate to the patient's body near the implant site of IMD 110 to improve the quality or security of communication between IMD 110 and external programmer 104. Communication between external programmer 104 and IMD 110 may occur during power transmission or separate from power transmission.

In some examples, IMD 110, in response to commands from external programmer 104, delivers electrical stimulation therapy (e.g., informed pulses and/or control pulses) according to a plurality of therapy stimulation programs to a target tissue site of the spinal cord 106 of patient 102 via electrodes (not depicted) on leads 108. In some examples, IMD 110 modifies therapy stimulation programs as therapy needs of patient 102 evolve over time. For example, the modification of the therapy stimulation programs may cause the adjustment of at least one parameter of the plurality of stimulation pulses. When patient 102 receives the same therapy for an extended period, the efficacy of the therapy may be reduced. In some cases, parameters of the plurality of stimulation pulses may be automatically updated.

As described herein, IMD 110 may be configured to detect ECAP signals which are representative of the number of nerve fibers activated by a delivered stimulation signal (e.g., a control pulse). Since the distance between electrodes and the target nerve changes in response to any of a number of movement-based aggressors, a characteristic value of one or more ECAP signals can be indicative of the presence of one or more aggressors when the one or more ECAP signals are detected by IMD 110. In one example, IMD 110 may deliver a plurality of control pulses defined by different parameter values and detect the respective ECAP signal elicited by each pulse. IMD 110 may determine a relationship between characteristic values from each ECAP signal (or across a plurality of consecutive ECAP signals) and the different parameter values of the control pulses, and this relationship may be different for each aggressor or category of similar aggressors. In one example, the relationship may be a curve of the characteristic values of the ECAP (e.g., an amplitude of the ECAP signal) vs. values of a stimulation parameter (e.g., the current amplitude of the respective control pulses) that elicited each ECAP signal from which the characteristic values were derived. Each aggressor or aggressor category may have a respective "signature" curve that varies in slope, shape, and/or intercept. In some examples, a gain value may be determined from the signature of the aggressor.

In this disclosure, efficacy of electrical stimulation therapy may be indicated by one or more characteristics (e.g. an amplitude of or between one or more peaks or an area under the curve of one or more peaks) of an action potential that is evoked by a control pulse delivered by IMD 110 (i.e., a characteristic value of the ECAP signal). Electrical stimulation therapy delivery by leads 108 of IMD 110 may cause neurons within the target tissue to evoke a compound action potential that travels up and down the target tissue, eventually arriving at sensing electrodes of IMD 110. Furthermore, stimulation may also elicit at least one ECAP signal, and ECAPs responsive to stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the control pulse at the beginning and/or end of each control pulse or each phase within the pulse. For example, a very high slew rate indicates a steep or even near-vertical edge of the pulse, and a low slew rate indicates a longer ramp up (or ramp down) in the amplitude of the control pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control pulses.

Some example techniques for adjusting stimulation parameter values for stimulation pulses (e.g., informed pulses and/or control pulses that may or may not contribute to therapy for the patient) are based on comparing the value of a characteristic of a measured ECAP signal to a target ECAP characteristic value. In response to delivering a control pulse defined by a set of stimulation parameter values, IMD 110, via two or more electrodes interposed on leads 108, senses electrical potentials of tissue of the spinal cord 106 of patient 102 to measure the electrical activity of the tissue. IMD 110 senses ECAPs from the target tissue of patient 102, e.g., with electrodes on one or more leads 108 and associated sense circuitry. In some examples, IMD 110 receives a signal indicative of the ECAP from one or more sensors, e.g., one or more electrodes and circuitry, internal or external to patient 102. Such an example signal may include a signal indicating an ECAP of the tissue of patient 102. Examples of the one or more sensors include one or more sensors configured to measure a compound action potential of patient 102, or a physiological effect indicative of a compound action potential. For example, to measure a physiological effect of a compound action potential, the one or more sensors may be an accelerometer, a pressure sensor, a bending sensor, a sensor configured to detect a posture of patient 102, a pulse oximeter, a cardiac sensor, an analyte sensor, or a sensor configured to detect a respiratory function or muscular activity of patient 102. However, in other examples, external programmer 104 receives a signal indicating a compound action potential in the target tissue of patient 102 and transmits a notification to IMD 110.

In the example of FIG. 1, IMD 110 is described as performing a plurality of processing and computing functions. However, external programmer 104 instead may perform one, several, or all of these functions. In this alternative example, IMD 110 functions to relay sensed signals to external programmer 104 for analysis, and external programmer 104 transmits instructions to IMD 110 to adjust the one or more parameters defining the electrical stimulation therapy based on analysis of the sensed signals. For example, IMD 110 may relay the sensed signal indicative of an ECAP to external programmer 104. External programmer 104 may compare the parameter value of the ECAP to the target ECAP characteristic value, and in response to the comparison, external programmer 104 may instruct IMD 110 to adjust one or more stimulation parameters that define the electrical stimulation informed pulses and, in some examples, control pulses, delivered to patient 102.

In some examples, the system changes the target ECAP characteristic value over a period of time, such as according to a change to a stimulation threshold (e.g., a perception threshold or detection threshold specific for the patient). The system may be programmed to change the target ECAP characteristic in order to adjust the intensity of informed pulses to provide varying sensations to the patient (e.g., increase or decrease the volume of neural activation). Although the system may change the target ECAP characteristic value, received ECAP signals may still be used by the system to adjust one or more parameter values of the informed pulses and/or control pulses in order to meet the target ECAP characteristic value.

One or more devices within system 100, such as IMD 110 and/or external programmer 104, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses (e.g., control pulses) having different amplitude values and control the sensing circuitry to detect, after delivery of each electrical stimulation pulse of the plurality of electrical stimulation pulses, a respective ECAP signal of the plurality of ECAP signals. The processing circuitry of IMD 110 may then determine, based on the plurality of ECAP signals, an aggressor or aggressor category, e.g., corresponding to a characteristic variability across the plurality of ECAP signals.

As described herein, IMD 110 may modulate or adjust one or more stimulation parameters that at least partially define electrical stimulation based on a detected aggressor or aggressor category. IMD 110 may use the detected aggressor or aggressor category to determine how to employ ECAP signals in a closed-loop feedback system for adjusting stimulation parameters that define informed pulses and/or control pulses. In one example, IMD 110 includes stimulation-generation circuitry configured to generate and deliver electrical stimulation to patient 102 according one or more sets of stimulation parameters (e.g., informed parameters and/or control parameters) that at least partially define the respective informed pulses and/or control pulses of the electrical stimulation. Each set of stimulation parameters may include at least one of an amplitude, a pulse width, a pulse frequency, or a pulse shape.

IMD 110 may also include sensing circuitry configured to sense an ECAP signal elicited by delivered electrical stimulation, such as a control pulse. IMD 110 may also include processing circuitry configured to control delivery of an informed pulses to patient 102 according to a first value of an informed stimulation parameter and determine a characteristic value of the ECAP signal detected from the control pulse. IMD 110 may also receive, from a sensor, input data indicative of the presence of one or more aggressors causing a variability across a plurality of sensed ECAP signals. In some examples, IMD 110 may then determine, based on the sensed ECAP signal(s) and/or the input data, a gain value for the stimulation parameter and adjust, based on the characteristic value of the ECAP signal and the gain value, the first value of the informed stimulation parameter to a second value of the informed stimulation parameter. In other examples, IMD 110 may additionally, or alternatively, adjust a target ECAP characteristic value or a threshold ECAP characteristic value based on the sensed ECAP signal(s) and/or the input data. IMD 110 may then control subsequent delivery of one or more informed stimulation pulses according to the second value of the informed stimulation parameter. In this manner, an informed parameter value that defines the next informed pulse was "informed" by the ECAP signal elicited by a control pulse.

In some examples, the processing circuitry of IMD 110 may be configured to adjust the first value of the informed parameter to the second value of the informed parameter by increasing or decreasing the informed parameter of the informed pulses based on a control policy associated with a detected aggressor or aggressor category. In addition, the processing circuitry may be configured to adjust a control parameter value for subsequent control pulses based on the control policy. As discussed herein, the control policy may represent a relationship between one or more parameters of delivered control pulses and a characteristic of ECAP signals. For example, the characteristic may be an amplitude of the ECAP signals (e.g., an amplitude between an N1 peak and a P2 peak of the ECAP signal), an area under one or more peaks of the ECAP signal, or any other metric indicative of the nerve activation that resulted in the ECAP signal.

When IMD 110 is configured to modulate stimulation pulses in order to maintain consistent nerve activation, such as increasing and decreasing a stimulation parameter to maintain a target ECAP characteristic value, IMD 110 may perform an example process. For example, IMD 110 may monitor an amplitude that is the characteristic value of the detected ECAP signal. IMD 110 may adjust the first value to the second value of the informed stimulation parameter by subtracting the amplitude from a target ECAP amplitude value for the patient to generate a differential amplitude. The differential amplitude is the difference between the detected amplitude from the ECAP signal and the target ECAP amplitude value. IMD 110 may then multiply the differential amplitude by the gain value that at least partially defines the control pulses to generate a differential value. The gain value may be a multiplier or fraction selected based on the detected aggressor or aggressor category. A larger gain value may be associated with aggressors for which the resulting change in distance between electrodes and the target nerve is larger (e.g., transient aggressors, in some but not all cases), because larger change in distance requires a corresponding larger change in stimulation pulse intensity to regain a target ECAP value in an appropriately short amount of time. IMD 110 may then add the differential value to a previous amplitude value (e.g., the amplitude value of the last control pulse that was delivered and elicited the ECAP signal) to generate the second value that at least partially defines the next control pulse to be delivered to patient 102. IMD 110 may then multiply the differential value by a scaling factor to generate an informed differential value representing how much the amplitude of the informed pulses needs to change. The scaling factor may be greater than one when the informed pulse amplitude is greater than the control pulse amplitude, and conversely, the scaling factor may be less than one when the informed pulse amplitude is less than the control pulse amplitude. IMD 110 can then add the informed differential value to the previous amplitude value of the informed pulses to generate a second value of the informed pulses for subsequent delivery to the patient.

In other examples, IMD 110 may not attempt to maintain consistent nerve activation by modulating stimulation pulses to achieve a target ECAP characteristic value. Instead, IMD 110 may monitor characteristic values of ECAP signals and only take action when the characteristic value exceeds a threshold ECAP characteristic value (or threshold change in ECAP characteristic value). Characteristic values exceeding the threshold ECAP characteristic values may be indicative of increased stimulation perception that may be above an uncomfortable threshold or pain threshold for the patient. Therefore, reducing stimulation pulse intensity when the characteristic value exceeds this level of stimulation may reduce the likelihood that patient 102 experiences any uncomfortable sensations that may occur as a result of any transient or cyclical movement, such as a posture change, sneeze, cough, heartbeat, respiration, etc. For example, IMD 110 may be configured to compare the characteristic value of the ECAP signal to a threshold ECAP characteristic value and determine that the characteristic value of the ECAP signal is greater than the threshold ECAP characteristic value. Responsive to determining that the characteristic value of the ECAP signal is greater than the threshold ECAP characteristic value, IMD 110 may be configured to decrease the first value of the informed stimulation parameter to the second value of the informed stimulation parameter for subsequent informed pulses to be delivered. Similarly, IMD 110 may be configured to decrease the value of a control stimulation parameter that defines subsequent control pulses to be delivered.

IMD 110 may continue to decrease the informed stimulation parameter value and/or the control stimulation parameter value as long as the ECAP characteristic value continues to exceed the threshold ECAP characteristic value. Once the informed and control stimulation parameters have been decreased, IMD 110 may attempt to increase the informed and control stimulation parameter values again back up to the predetermined first value intended for the informed stimulation pulses and/or control stimulation pulses. IMD 110 may be configured to determine other characteristic values of subsequent ECAP signals elicited from control stimulation pulses delivered after sensing the first ECAP signal. In response to determining that another characteristic value of the subsequent ECAP signals decreases below the threshold ECAP characteristic value, IMD 110 may then increase the value of the informed and/or control stimulation parameter back up to a value limited to be less-than-orequal-to the first value (e.g., back up to the predetermined value for the informed and/or control stimulation pulses that may be determined by a set of stimulation parameters or therapy program). In some examples, IMD 110 may iteratively increase the informed and/or control stimulation parameter values until the first value, or original value, is again reached after the characteristic values of the ECAP signal remain below the threshold ECAP characteristic value (or change in value). IMD 110 may increase the informed and/or control stimulation parameter values at a slower rate than the informed and/or control stimulation parameter values are decreased, but, in other examples, IMD 110 may increase and decrease the informed and/or control stimulation parameters at the same rates.

A detected aggressor (or aggressor category) may be one aggressor of a plurality of aggressors. Different aggressors or categories of aggressors may pose different challenges to closed-loop adjustment based on determined ECAP values. In some examples, IMD 110 may select, based on the detected aggressor, the gain value from a plurality of gain values associated with respective aggressors or aggressor categories. The gain value may represent at least one of an increment rate (e.g., how fast IMD 110 should increase the stimulation parameter value) or a decrement rate (e.g., how slow IMD 110 should decrease the stimulation parameter value) for the control stimulation parameter (or the informed stimulation parameter in some examples) that at least partially defines the control stimulation pulses. In other examples, the gain value may represent a particular magnitude that IMD 110 should increment or decrement a previous parameter value of control pulses and/or informed pulses each time IMD 110 increases or decrease the parameter value. This particular magnitude may effectively result in a rate of change at which IMD 110 can adjust a stimulation parameter value. In addition, or alternatively, IMD 110 may select the target ECAP characteristic value or the threshold ECAP characteristic value according to the detected aggressor or aggressor type of category. A patient may or may not benefit from aggressor-specific target ECAP values or threshold ECAP characteristic values. In some examples, IMD 110 may select a gain based on the aggressor type and another feature, such as posture which may have a respective gain value associated with the control policy for the determined aggressor or aggressor category.

IMD 110 may determine the presence of one or more aggressors at predetermined intervals or during predetermined periods of time. In some examples, IMD 110 may determine the aggressor(s) in response to a trigger event, such as a patient-requested change in stimulation therapy, a sensed event representative of a patient condition such as pain, or any other triggers. In some examples, IMD 110 may modulate aggressor-determination frequency based on whether or not aggressors are detected. For example, IMD 110 may determine, based on an above-threshold variation in sensed ECAP signal, that one or more aggressors is likely present to cause the variation. Additionally or alternatively, IMD 110 may determine, based on input data from one or more sensors, that one or more aggressors is likely affecting the amplitude of the sensed ECAP signal. Responsive to determining that one or more aggressors is present, IMD 110 may change the ECAP-sensing frequency and/or aggressor-determination frequency. IMD 110 may increase aggressor-determination frequency when more aggressors are expected and decrease aggressor-determination frequency when fewer aggressors are expected. "Sensing frequency" or "determination frequency" may refer to sensor-sampling frequency and/or frequency at which processing circuitry analyzes data obtained from one or more sensors (including the ECAP signal obtained from sensing electrodes). In this manner, IMD 110 may modulate sensing frequency or otherwise reduce processing tasks to conserve power consumption.

As discussed herein, some example techniques for adjusting informed stimulation parameter values and/or control stimulation parameter values for electrical stimulation signals are based on comparing the value of a characteristic of a plurality of ECAP signals to a target ECAP characteristic value, or based on using control parameter values at a determined target ECAP characteristic to inform adjustment of one or more control parameter values and/or informed parameter values to maintain the target ECAP according to known relationships between parameters. For example, during delivery of an electrical stimulation signal, IMD 110, via two or more electrodes interposed on leads 108, senses electrical potentials of tissue of the spinal cord 106 of patient 102 to measure the electrical activity of the tissue. IMD 110 senses ECAPs from the target tissue of patient 102, e.g., with electrodes on one or more leads 108 and associated sensing circuitry. In some examples, IMD 110 receives a signal indicative of the ECAP from one or more sensors, e.g., one or more electrodes and circuitry, internal or external to patient 102. Such an example signal may include a signal indicating an ECAP of the tissue of the patient 102. Examples of the one or more sensors include sensors that can measure a compound action potential of the patient 102, a physiological effect indicative of a compound action potential, or any other input indicative of the presence of an aggressor currently affecting patient 102. For example, to measure a physiological effect of a compound action potential, the one or more sensors may be an accelerometer, a pressure sensor, a bending sensor, a sensor that can detect a posture of patient 102, or a sensor that can detect a respiratory function of patient 102. However, in other examples, external programmer 104 receives a signal indicating a compound action potential in the target tissue of patient 102 and transmits a notification to IMD 110.

IMD 110 of FIG. 1 is described herein as performing a plurality of processing and computing functions. However, external programmer 104 instead may perform one, several, or all of these functions. In this alternative example, IMD 110 functions to relay sensed signals to external programmer 104 for analysis, and external programmer 104 transmits instructions to IMD 110 to adjust the one or more parameters defining the electrical stimulation signal based on analysis of the sensed signals. For example, IMD 110 may relay a sensed signal indicative of an ECAP to external programmer 104. External programmer 104 may compare the parameter value of the ECAP to the target ECAP characteristic value, and in response to the comparison, external programmer 104 may instruct IMD 110 to adjust one or more parameters that define the electrical stimulation signal.

In the example techniques described herein, the informed stimulation parameter values, control stimulation parameter values, posture states, and the target ECAP characteristic values (e.g., values of the ECAP indicative of target stimulation intensity) may be initially set at the clinic but may be set and/or adjusted at home by patient 102. Once the target ECAP characteristic values are set, the example techniques allow for automatic adjustment of informed and/or control stimulation parameters to maintain consistent volume of neural activation and consistent perception of therapy for the patient when the electrode-to-neuron distance changes. The ability to change the stimulation parameter values may also allow the therapy to have long-term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 102.

In some examples, the system may change the target ECAP characteristic value over a period of time (e.g., based on a detected aggressor or change in patient conditions). The system may be programmed to change the target ECAP characteristic in order to adjust the intensity of the informed pulses and/or control pulses to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a "wave" or other sensation that may provide therapeutic relief for the patient. The maximum target ECAP characteristic value, the minimum target ECAP characteristic value, and the predetermined frequency may be stored in the memory of IMD 110 and may be updated in response to a signal from external programmer 104 (e.g., a user request to change the values stored in the memory of IMD 110). In other examples, the target ECAP characteristic value may be programmed to steadily increase or steadily decrease to a baseline target ECAP characteristic value over a period of time. In other examples, external programmer 104 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more informed and/or control parameter values of the electrical stimulation signal in order to meet the target ECAP characteristic value.

Although in one example IMD 110 takes the form of an SCS device, in other examples, IMD 110 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as non-limiting examples.

Figure 2:
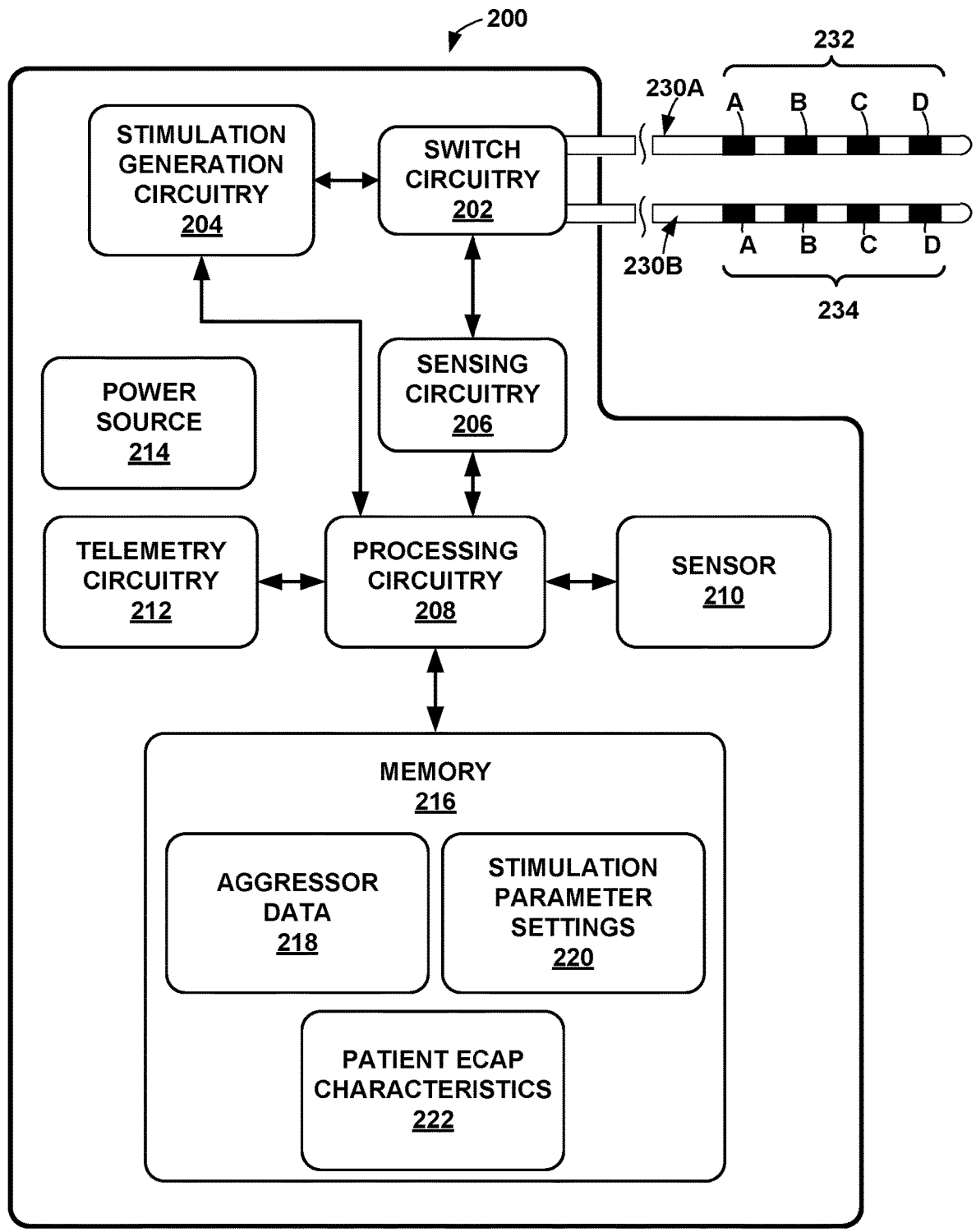
FIG. 2 is a block diagram of the example IMD of FIG. 1.

FIG. 2 is a block diagram of an example IMD 200, which may be an example of IMD 110 of FIG. 1. In the example shown in FIG. 2, IMD 200 includes switch circuitry 202, stimulation-generation circuitry 204, sensing circuitry 206, processing circuitry 208, sensor 210, telemetry circuitry 212, power source 214, and memory 216. Each of these circuits may be or may include programmable or fixed-function circuitry that can perform the functions attributed to respective circuitry. For example, processing circuitry 208 may include fixed-function or programmable circuitry, stimulation-generation circuitry 204 may include circuitry that can generate electrical stimulation signals such as pulses or continuous waveforms on one or more channels, sensing circuitry 206 may include sensing circuitry for sensing signals, and telemetry circuitry 212 may include telemetry circuitry for transmission and reception of signals. Memory 216 may store computer-readable instructions that, when executed by processing circuitry 208, cause IMD 200 to perform various functions described herein. Memory 216 may be a storage device or other non-transitory medium.

In the example shown in FIG. 2, memory 216 stores aggressor data 218, which may include one or more types of aggressors or aggressor categories, and corresponding characteristic ECAP signals (e.g., signal parameters) associated with or indicative of the presence of one or more of the aggressors and/or aggressor categories. A set of pre-established aggressor definitions may be stored in aggressor data 218. An aggressor definition may be modified based on user therapy adjustments and/or other input data. In some cases, the aggressor or aggressor category may be expanded and split, or instead, may be reduced in size based on input data. The aggressor definitions can be automatically updated or can be updated by a patient, including creating new aggressor types and aggressor categories. Aggressor categories may include, for example, transient aggressors and cyclic aggressors. Specific types of transient aggressors may include, as non-limiting examples, a change in posture or other physical movement of the body of a patient, or an unintentional movement such as a cough, sneeze, a rotation, extension, or flexion of the patient's cervical spine, and a jolt from driving over a pothole. Specific types of cyclic aggressors may include, as non-limiting examples, a heartbeat, respiration, or a digestive cycle of a patient.

Memory 216 may store stimulation-parameter settings 220 within memory 216 or within separate areas (e.g., partitions) of memory 216. Each stored stimulation-parameter setting 220 defines values for one or more sets of electrical-stimulation parameters (e.g., an informed stimulation parameter set and a control stimulation parameter set), such as pulse amplitude, pulse width, pulse frequency, electrode combination, pulse-burst rate, pulse-burst duration, and/or waveform shape. Stimulation-parameter settings 220 may also include additional information such as instructions regarding delivery of electrical stimulation signals based on stimulation parameter relationship data, which can include relationships between two or more stimulation parameters based upon data from electrical stimulation signals delivered to patient 102 or data transmitted from external programmer 104. The stimulation parameter relationship data may include measurable aspects associated with stimulation, such as an ECAP characteristic value. Stimulation parameter settings 220, or another portion of memory 216, may include instructions on how processing circuitry 208 can modulate informed stimulation parameters and/or control stimulation parameters based on the detected posture state and/or at least one of a target ECAP characteristic value or a threshold ECAP characteristic value, as described herein.

Memory 216 also stores patient ECAP characteristics 222 which may include target ECAP characteristics and/or threshold ECAP characteristic values determined for the patient and/or a history of measured ECAP characteristic values for the patient. Instead of, or in addition to stimulation parameter settings 220, memory 216 may include gain values that processing circuitry 208 may use to modulate informed and/or control stimulation pulses as described herein. In other examples, stimulation parameter settings 220 may include information regarding relationships between ECAP characteristics and control stimulation parameters for one or more aggressors or aggressor categories.

Accordingly, in some examples, stimulation generation circuitry 204 generates electrical stimulation signals (e.g., informed pulses and control pulses) in accordance with the electrical stimulation parameters noted above. Other ranges of stimulation parameter values may also be useful and may depend on the target stimulation site within patient 102. While stimulation pulses are described, stimulation signals may be of any form, such as continuous-time signals (e.g., sine waves) or the like. Switch circuitry 202 may include one or more switch arrays, one or more multiplexers, one or more switches (e.g., a switch matrix or other collection of switches), or other electrical circuitry configured to direct stimulation signals from stimulation generation circuitry 204 to one or more of electrodes 232, 234, or directed sensed signals from one or more of electrodes 232, 234 to sensing circuitry 206. In other examples, stimulation generation circuitry 204 and/or sensing circuitry 206 may include sensing circuitry to direct signals to and/or from one or more of electrodes 232, 234, which may or may not also include switch circuitry 202.

Sensing circuitry 206 may be configured to monitor signals from any combination of electrodes 232, 234. In some examples, sensing circuitry 206 includes one or more amplifiers, filters, and analog-to-digital converters (ADCs). Sensing circuitry 206 may be used to sense physiological signals, such as ECAPs. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver control stimulation pulses and/or informed stimulation pulses. Alternatively, in other cases, the particular combination of electrodes used for sensing ECAPs includes at least one of the same electrodes as a set of electrodes used to deliver informed and/or control stimulation pulses to patient 102. Sensing circuitry 206 may provide signals to an analog-to-digital converter, for conversion into a digital signal for processing, analysis, storage, or output by processing circuitry 208.

Processing circuitry 208 may include any one or more of a microprocessor, a controller, a digital signal processor (DSP), an application specific integrated circuit (ASIC), a field-programmable gate array (FPGA), discrete logic circuitry, or any other processing circuitry can provide the functions attributed to processing circuitry 208 herein may be embodied as firmware, hardware, software or any combination thereof. Processing circuitry 208 controls stimulation generation circuitry 204 to generate electrical stimulation signals according to stimulation parameter settings 220 stored in memory 216 to apply stimulation parameter values, such as pulse amplitude, pulse width, pulse frequency, and waveform shape of each of the electrical stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 208 also controls stimulation generation circuitry 204 to generate and apply the electrical stimulation signals to selected combinations of electrodes 232, 234. In some examples, stimulation generation circuitry 204 includes a switch circuit (instead of, or in addition to, switch circuitry 202) that may couple stimulation signals to selected conductors within leads 230, which, in turn, deliver the stimulation signals across selected electrodes 232, 234. Such a switch circuit may be a switch array, switch matrix, multiplexer, or any other type of switch circuitry can selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 204 does not include a switch circuit and switch circuitry 202 does not interface between stimulation generation circuitry 204 and electrodes 232, 234. In these examples, stimulation generation circuitry 204 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 204, e.g., via switch circuitry 202 and/or switch circuitry of the stimulation generation circuitry 204, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 204 and processing circuitry 208 in FIG. 2, in other examples, sensing circuitry 206 may be in a separate housing from IMD 200 and may communicate with processing circuitry 208 via wired or wireless communication techniques.

In some examples, one or more of electrodes 232 and 234 may be suitable for sensing ECAPs. For instance, electrodes 232 and 234 may sense the voltage amplitude of a portion of the ECAP signals, where the sensed voltage amplitude is a characteristic the ECAP signal.

Memory 216 may be configured to store information within IMD 200 during operation. Memory 216 may include a computer-readable storage medium or computer-readable storage device. In some examples, memory 216 includes one or more of a short-term memory or a long-term memory. Memory 216 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, memory 216 is used to store data indicative of instructions for execution by processing circuitry 208. As discussed herein, memory 216 can store aggressor data 218, stimulation parameter settings 220, and patient ECAP characteristics 222.

Sensor 210 may include one or more sensing elements that sense values of a respective patient parameter. As described, electrodes 232 and 234 may be the electrodes that sense, via sensing circuitry 206, a value of the ECAP indicative of a target stimulation intensity at least partially caused by a set of control stimulation parameter values. Sensor 210 may include one or more accelerometers, optical sensors, chemical sensors (e.g., analyte sensors), temperature sensors, pressure sensors, pulse oximetry sensors, muscular activity sensors, cardiac sensors, respiratory sensors, gastrointestinal sensors, or any other types of sensors. Sensor 210 may output patient parameter values that may be used as feedback to control delivery of electrical stimulation signals. IMD 200 may include additional sensors within the housing of IMD 200 and/or coupled via one of leads 108 or other leads. In addition, IMD 200 may receive sensor signals wirelessly from remote sensors via telemetry circuitry 212, for example. In some examples, one or more of these remote sensors may be external to patient (e.g., carried on the external surface of the skin, attached to clothing, or otherwise positioned external to the patient). In some examples, signals from sensor 210, or other similar input data, may indicate the presence of one or more aggressors or aggressor categories or likelihood that a certain type of aggressor will be present according to the input data, and processing circuitry 208 may select stimulation gain values, target and/or threshold ECAP characteristic values, or the like, according to the input data that may be associated with particular detected aggressors or aggressor categories. In this manner, processing circuitry 208 may be configured to determine a dominant aggressor or aggressor category currently affecting observed ECAP values via modification of the distance between electrodes 232, 234 and the target region of the patient (e.g., the spinal cord).

Telemetry circuitry 212 supports wireless communication between IMD 200 and an external programmer (not shown in FIG. 2) or another computing device under the control of processing circuitry 208. Processing circuitry 208 of IMD 200 may receive, as updates to programs, values for various stimulation parameters such as amplitude and electrode combination (e.g., for informed pulses and/or control pulses), from the external programmer via telemetry circuitry 212. Updates to stimulation parameter settings 220 and input efficacy threshold settings 226 may be stored within memory 216. Telemetry circuitry 212 in IMD 200, as well as telemetry circuits in other devices and systems described herein, such as the external programmer, may accomplish communication by radiofrequency (RF) communication techniques. In addition, telemetry circuitry 212 may communicate with an external medical device programmer (not shown in FIG. 2) via proximal inductive interaction of IMD 200 with the external programmer. The external programmer may be one example of external programmer 104 of FIG. 1. Accordingly, telemetry circuitry 212 may send information to the external programmer on a continuous basis, at periodic intervals, or upon request from IMD 110 or the external programmer.

Power source 214 delivers operating power to various components of IMD 200. Power source 214 may include a rechargeable or non-rechargeable battery and a power-generation circuit to produce the operating power. Recharging may be accomplished through proximal inductive interaction between an external charger and an inductive charging coil within IMD 200. In other examples, traditional primary cell batteries may be used. In some examples, processing circuitry 208 may monitor the remaining charge (e.g., voltage) of power source 214 and select stimulation parameter values that may deliver similarly effective therapy at lower power-consumption levels when needed to extend the operating time of power source 214. For example, power source 214 may switch to a lower pulse frequency based on the relationships of parameters that may provide similar ECAP characteristic values.

According to the techniques of the disclosure, stimulation-generation circuitry 204 of IMD 200 receives, via telemetry circuitry 212, instructions to deliver electrical stimulation according to stimulation parameter settings 220 to a target tissue site of the spinal cord of the patient via a plurality of electrode combinations of electrodes 232, 234 of leads 230 and/or a housing of IMD 200. Each electrical stimulation signal may elicit an ECAP that is sensed by sensing circuitry 206 via electrodes 232 and 234. Processing circuitry 208 may receive, via an electrical signal sensed by sensing circuitry 206, information indicative of an ECAP signal (e.g., a numerical value indicating a characteristic of the ECAP in electrical units such as voltage or power) produced in response to the electrical stimulation signal(s). Stimulation parameter settings 220 may be updated according to the ECAPs recorded at sensing circuitry 206 according to the following techniques.

Generally, the pulse width of informed pulses are greater than the pulse width of control pulses. This difference in pulse width may allow ECAPs elicited from the control pulses to be detectable by the system when the longer pulse widths of the informed pulses prevent elicited ECAPs, or at least some portion of the elicited ECAPs, from being detectable. In some examples, the plurality of informed stimulation pulses are defined by an informed pulse width greater than approximately 300 microseconds and less than approximately 1000 microseconds, while the plurality of control stimulation pulses are defined by a control pulse width less than approximately 300 microseconds. In one example, the plurality of informed pulses each have a pulse width of greater than approximately 300 μs and less than approximately 2000 μs (i.e., 2 milliseconds). In some examples, the informed pulse width is greater than approximately 300 μs and less than approximately 900 μs. In another example, the informed pulse width is greater than approximately 300 μs and less than approximately 500 μs. In one example, the informed pulses have a pulse width of approximately 450 μs and a pulse frequency of approximately 60 Hertz. Amplitude (current and/or voltage) for the pulses may be between approximately 0.5 mA (or volts) and approximately 10 mA (or volts), although amplitude may be lower or greater in other examples.

In one example, the predetermined pulse frequency of the plurality of informed pulses may be less than approximately 400 Hertz. In some examples, the predetermined pulse frequency of the plurality of pulses may be between approximately 50 Hertz and 70 Hertz. In one example, the predetermined pulse frequency of the plurality of pulses may be approximately 60 Hertz. However, the informed pulses may have frequencies greater than 400 Hertz or less than 50 Hertz in other examples. In addition, the informed pulses may be delivered in bursts of pulses, with interburst frequencies of the informed pulses being low enough such that a sensed ECAP elicited by a control pulse can still fit within the window between consecutive pulses delivered within the burst of pulses. In any example, processing circuity 208 may be configured to detect ECAPs elicited from respective control stimulation pulses.

The pulse width of the control pulses may be shorter than the pulse width of the informed pulses to reduce or prevent a sensed electrical artifact from control pulses from obscuring the ECAP signals (put another way, the pulse width of the informed pulses may be longer than the pulse width of the control pulses). For example, the control pulses may be less than approximately 300 microseconds (μs). In one example, the control pulse may be a bi-phasic pulse having a positive phase of approximately 100 μs and a negative phase of approximately 100 μs separated by an interphase interval of approximately 30 μs. In this manner, stimulation electrodes at one end of a lead may deliver the control pulse and electrodes at the other end of the same lead may sense the ECAP signal without, or with minimal, interference from the control pulse itself. In general, the term "pulse width" herein refers to the collective duration of every phase, and interphase interval when appropriate, of a single pulse. A single pulse may include a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 μs, a negative phase lasting 100 μs, and an interphase interval lasting 30 μs defines a pulse width of 230 μs).

Processing circuitry 208 may be configured to compare one or more characteristics of a plurality of ECAPs sensed by sensing circuitry 206 with target ECAP characteristics stored in memory 216 (e.g., patient ECAP characteristics 222). For example, processing circuitry 208 can determine the amplitude of each ECAP signal received at sensing circuitry 206, and processing circuitry 208 can determine the representative amplitude of at least one respective ECAP signal and compare the representative amplitude of a series of ECAP signals to a target ECAP characteristic value.

In other examples, processing circuitry 208 may use the representative amplitude of the at least one respective ECAP to change other parameters of stimulation pulses (e.g., informed pulses and/or control pulses) to be delivered, such as pulse width, pulse frequency, and pulse shape. All of these parameters may contribute to the intensity of the stimulation pulses, and changing one or more of these parameter values may effectively adjust the stimulation pulse intensity to compensate for a changing distance between the stimulation electrodes and the nerves, as caused by one or more aggressors and as indicated by the characteristic (e.g., a representative amplitude or curve shape or pattern) of the ECAP signals.

In some examples, leads 230 may be linear 8-electrode leads (not pictured); sensing and stimulation delivery may each be performed using a different set of electrodes of leads 230. In a linear 8-electrode lead, each electrode may be numbered consecutively from "0" through "7." For instance, a pulse may be generated using Electrode 1 as a cathode and Electrodes 0 and 2 as anodes (e.g., a guarded cathode), and a respective ECAP signal may be sensed using Electrodes 6 and 7, which are located on the opposite end of the electrode array. This strategy may reduce or minimize the interference of the stimulation pulse with the sensing of the respective ECAP. Other electrode combinations may be implemented, and the electrode combinations may be changed using the patient programmer via telemetry circuitry 212. For example, stimulation electrodes and sensing electrodes may be positioned closer together. Shorter pulse widths for the nontherapeutic pulses may allow the sensing electrodes to be closer to the stimulation electrodes.

In one example, sensor 210 may detect an aggressor, including activity (e.g., a change in posture of the patient), a cough, a sneeze, a heartbeat, etc. Processing circuitry 208 may receive an indication of the presence of the aggressor from sensor 210, and processing circuitry 208 can initiate or change the delivery of the plurality of pulses according to stimulation parameter settings 220. For example, processing circuitry 208 may increase the amplitude and/or frequency of pulse delivery and respective ECAP sensing in response to receiving input data that includes an indication that the patient activity has increased (or other transient aggressor), which may indicate that the distance between electrodes and nerves will likely change. Alternatively, processing circuitry 208 may decrease the amplitude and/or frequency of pulse delivery and respective ECAP sensing in response to receiving an indication that the patient activity has decreased. In some examples, one or more therapy parameters (e.g., frequency, amplitude, slew rate, pulse width, or the like) may be adjusted (e.g., increased or decreased) in response to receiving an indication of an aggressor or aggressor category. Processing circuitry 208 can update aggressor data 218 according to the signal received from sensor 210.

Figure 3:
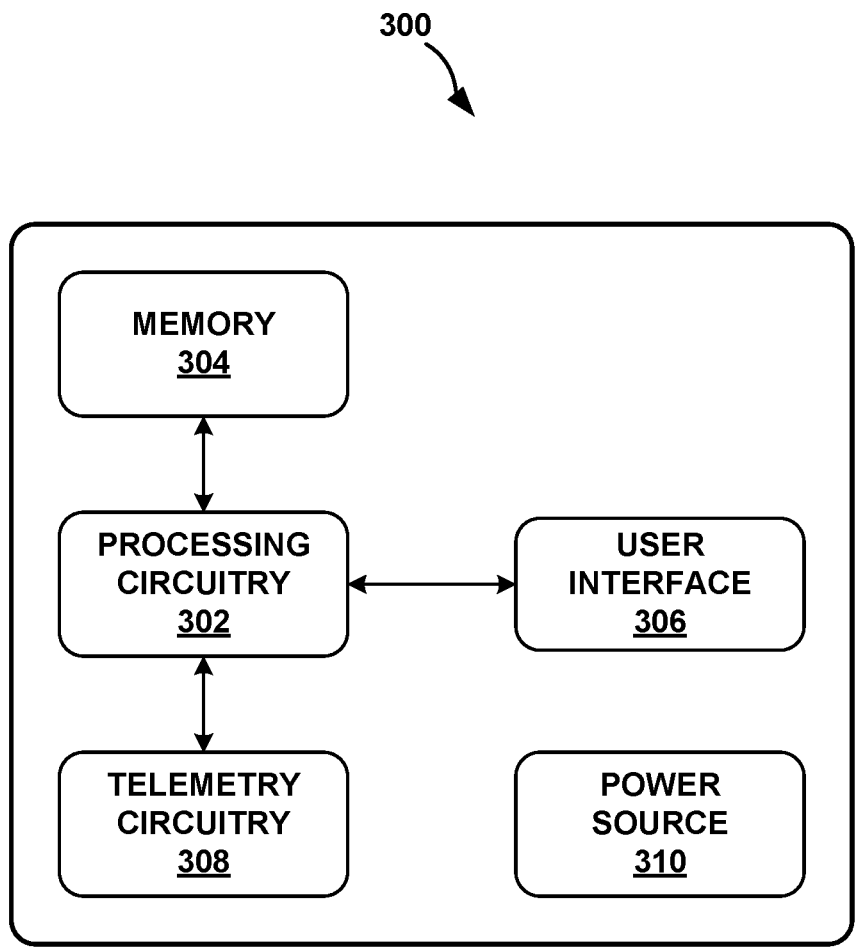
FIG. 3 is a block diagram of the example external programmer of FIG. 1.

FIG. 3 is a block diagram of an example external programmer 300, which may be an example of external programmer 104 of FIG. 1. Although programmer 300 may generally be described as a hand-held device, external programmer 300 may be a larger portable device or a more stationary device. In addition, in some examples, external programmer 300 may be included as part of an external charging device or may include the functionality of an external charging device. As illustrated in FIG. 3, external programmer 300 may include processing circuitry 302, memory 304, user interface 306, telemetry circuitry 308, and power source 310. Storage device 304 may store instructions that, when executed by processing circuitry 302, cause processing circuitry 302 and external programmer 300 to provide the functionality ascribed to external programmer 300 throughout this disclosure. Each of these components, circuitry, or modules, may include electrical circuitry that can perform some, or all of the functionality described herein. For example, processing circuitry 302 may include processing circuitry to perform the processes discussed with respect to processing circuitry 302.

In general, programmer 300 comprises any suitable arrangement of hardware, alone or in combination with software and/or firmware, to perform the techniques attributed to programmer 300, and processing circuitry 302, user interface 306, and telemetry circuitry 308 of programmer 300. In various examples, programmer 300 may include one or more processors, such as one or more microprocessors, DSPs, ASICs, FPGAs, or any other equivalent integrated or discrete logic circuitry, as well as any combinations of such components. Programmer 300 also, in various examples, may include a memory 304, such as RAM, ROM, PROM, EPROM, EEPROM, flash memory, a hard disk, a CD-ROM, comprising executable instructions for causing the one or more processors to perform the actions attributed to them. Moreover, although processing circuitry 302 and telemetry circuitry 308 are described as separate, in some examples, processing circuitry 302 and telemetry circuitry 308 are functionally integrated. In some examples, processing circuitry 302 and telemetry circuitry 308 correspond to individual hardware units, such as ASICs, DSPs, FPGAs, or other hardware units.

Memory 304 (e.g., a storage device) may store instructions that, when executed by processing circuitry 302, cause processing circuitry 302 and programmer 300 to provide the functionality ascribed to programmer 300 throughout this disclosure. For example, memory 304 may include instructions that cause processing circuitry 302 to obtain a stimulation parameter setting from memory, select a spatial electrode movement pattern, or receive a user input and send a corresponding command to programmer 300, or instructions for any other functionality. In addition, memory 304 may include a plurality of stimulation parameter settings, where each setting includes a parameter set that defines electrical stimulation. Memory 304 may also store data received from a medical device (e.g., IMD 110). For example, memory 304 may store ECAP-related data recorded at a sensing circuitry of the medical device, and memory 304 may also store data from one or more sensors of the medical device (or other external sensors).

User interface 306 may include a button or keypad, lights, a speaker for voice commands, a display, such as a liquid crystal (LCD), light-emitting diode (LED), or organic light-emitting diode (OLED). In some examples the display may be a touch screen. User interface 306 can display any information related to the delivery of electrical stimulation, identified patient behaviors, sensed patient parameter values, patient behavior criteria, or any other such information. External programmer 300 may receive user input (e.g., indication of when the patient changes posture states) via user interface 306. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation. In other examples, user interface 306 may receive input from the patient and/or clinician regarding efficacy of the therapy, such as binary feedback, numerical ratings, textual input, etc. In some examples, processing circuitry 302 may interpret patient requests to change therapy as negative feedback regarding the current parameter values used to define therapy.

Telemetry circuitry 308 may support wireless communication between the medical device and programmer 300 under the control of processing circuitry 302. Telemetry circuitry 308 can communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 300 and IMD 110 include RF communication according to the 902.11 or Bluetooth specification sets or other standard or proprietary telemetry protocols. In this manner, other external devices may be capable of communicating with programmer 300 without needing to establish a secure wireless connection. As described herein, telemetry circuitry 308 can transmit a spatial electrode movement pattern or other stimulation parameter values to IMD 110 for delivery of electrical stimulation.

In some examples, selection of stimulation parameter settings (e.g., informed parameter values and/or control parameter values) may be transmitted to the medical device for delivery to the patient. In other examples, stimulation parameter settings may include medication, activities, or other instructions that the patient must perform themselves or a caregiver perform for patient 102. In some examples, external programmer 300 may provide visual, audible, and/or tactile notifications that indicate there are new instructions. External programmer 300 may require receiving user input acknowledging that the instructions have been completed in some examples.

According to the techniques of the disclosure, user interface 306 of external programmer 300 receives an indication from a clinician instructing a processor of the medical device to update one or more patient aggressor settings, gain values, or stimulation parameter settings. Updating the aggressor settings and gain value settings may cause the stimulation parameter settings to update as well, including changing one or more parameter values of the informed stimulation pulses delivered by the medical device according to the settings, such as pulse amplitude, pulse width, pulse frequency, electrode combination, and/or waveform shape. Gain values may be based upon sensed ECAP signals, aggressor data, and stimulation parameter data, in some examples. User interface 306 may also receive instructions from the clinician commanding any electrical stimulation.

Power source 310 can deliver operating power to various components of programmer 300. Power source 310 may be the same as or substantially similar to power source 214. Power source 310 may include a battery and a power generation circuit to produce the operating power. In some examples, the battery is rechargeable to allow extended operation. Recharging may be accomplished by electrically coupling power source 310 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
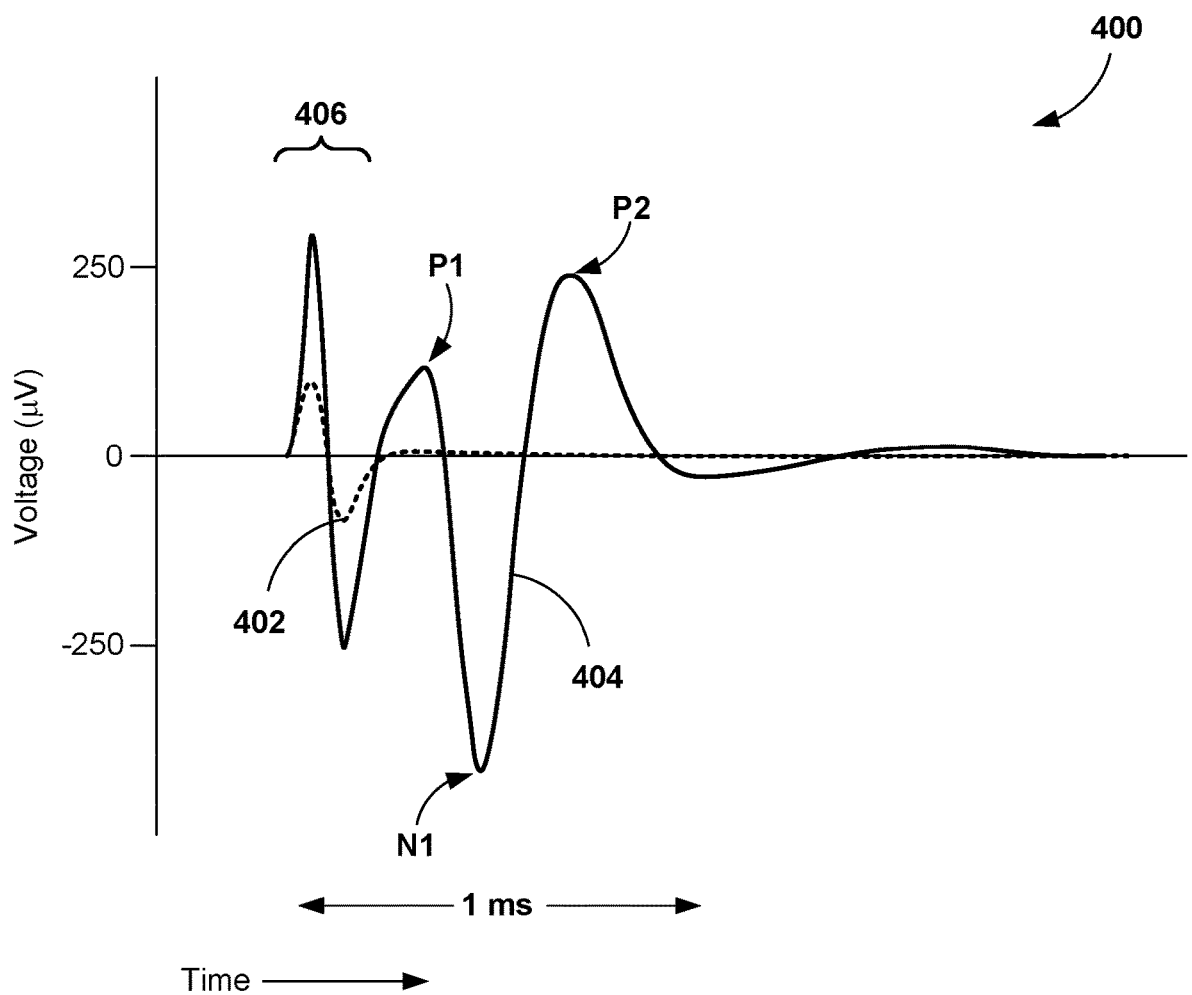
FIG. 4 is a graph of an example ECAP signal sensed from a stimulation pulse.

FIG. 4 is a graph 400 of an example of ECAP signals sensed for respective stimulation pulses (e.g., a control pulse). As shown in FIG. 4, graph 400 shows example ECAP signal 402 (dotted line) and ECAP signal 404 (solid line). Each of ECAP signals 402 and 404 may be sensed from control pulses that were delivered from a guarded cathode and bi-phasic pulses including an interphase interval between each positive and negative phase of the pulse. The guarded cathode of the stimulation electrodes is located at the end of an 8-electrode lead while two sensing electrodes are provided at the other end of the 8-electrode lead. ECAP signal 402 illustrates the voltage amplitude sensed as a result from a sub-threshold stimulation pulse. Peaks 406 of ECAP signal 402 are detected and represent the artifact of the delivered pulse. However, no propagating signal is detected after the artifact in ECAP signal 404 because the pulse was sub-threshold.

In contrast to ECAP signal 402, ECAP signal 404 represents the voltage amplitude detected from a supra-threshold stimulation pulse. Peaks 406 of ECAP signal 404 are detected and represent the artifact of the delivered pulse. After peaks 406, ECAP signal 404 also includes peaks P1, N1, and P2, which are three peaks representative of propagating action potentials from an ECAP. The example duration of the artifact and peaks P1, N1, and P2 is approximately 1 millisecond (ms). When detecting the ECAP of ECAP signal 404, different characteristics may be identified. For example, the characteristic of the ECAP may be the amplitude between N1 and P2. This N1-P2 amplitude can be detected even if the artifact impinges on P1, a relatively large signal, and the N1-P2 amplitude may be minimally affected by electronic drift in the signal. In other examples, the characteristic of the ECAP used to control pulses may be an amplitude of P1, N1, or P2 with respect to neutral or zero voltage. In some examples, the characteristic of the ECAP used to control pulses may be a sum of two or more of peaks P1, N1, or P2. In other examples, the characteristic of ECAP signal 404 may be the area under one or more of peaks P1, N1, and/or P2. In other examples, the characteristic of the ECAP may be a ratio of one of peaks P1, N1, or P2 to another one of the peaks. In some examples, the characteristic of the ECAP may be a slope between two points in the ECAP signal, such as the slope between N1 and P2. In other examples, the characteristic of the ECAP may be the time between two points of the ECAP, such as the time between N1 and P2. The time between two points in the ECAP signal may be referred to as a latency of the ECAP and may indicate the types of fibers being captured by the pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal increases with increased amplitude of the pulse, as long as the pulse amplitude is greater than the threshold such that nerves depolarize and propagate the signal. The target ECAP characteristic (e.g., the target ECAP amplitude) may be determined from the ECAP signal detected from a pulse when pulses are determined to deliver effective therapy to the patient. The ECAP signal thus is representative of the distance between the stimulation electrodes and the nerves appropriate for the stimulation parameter values of the pulses delivered at that time. Therefore, IMD 110 may attempt to use detected changes to the measured ECAP characteristic value to change stimulation pulse parameter values and maintain the target ECAP characteristic value during stimulation pulse delivery (e.g., informed pulses and/or control pulses). Alternatively, IMD 110 may attempt to prevent undesirable stimulation intensity by decreasing stimulation pulse intensity in response to the ECAP characteristic value exceeding a threshold ECAP characteristic value.

Figure 5A:
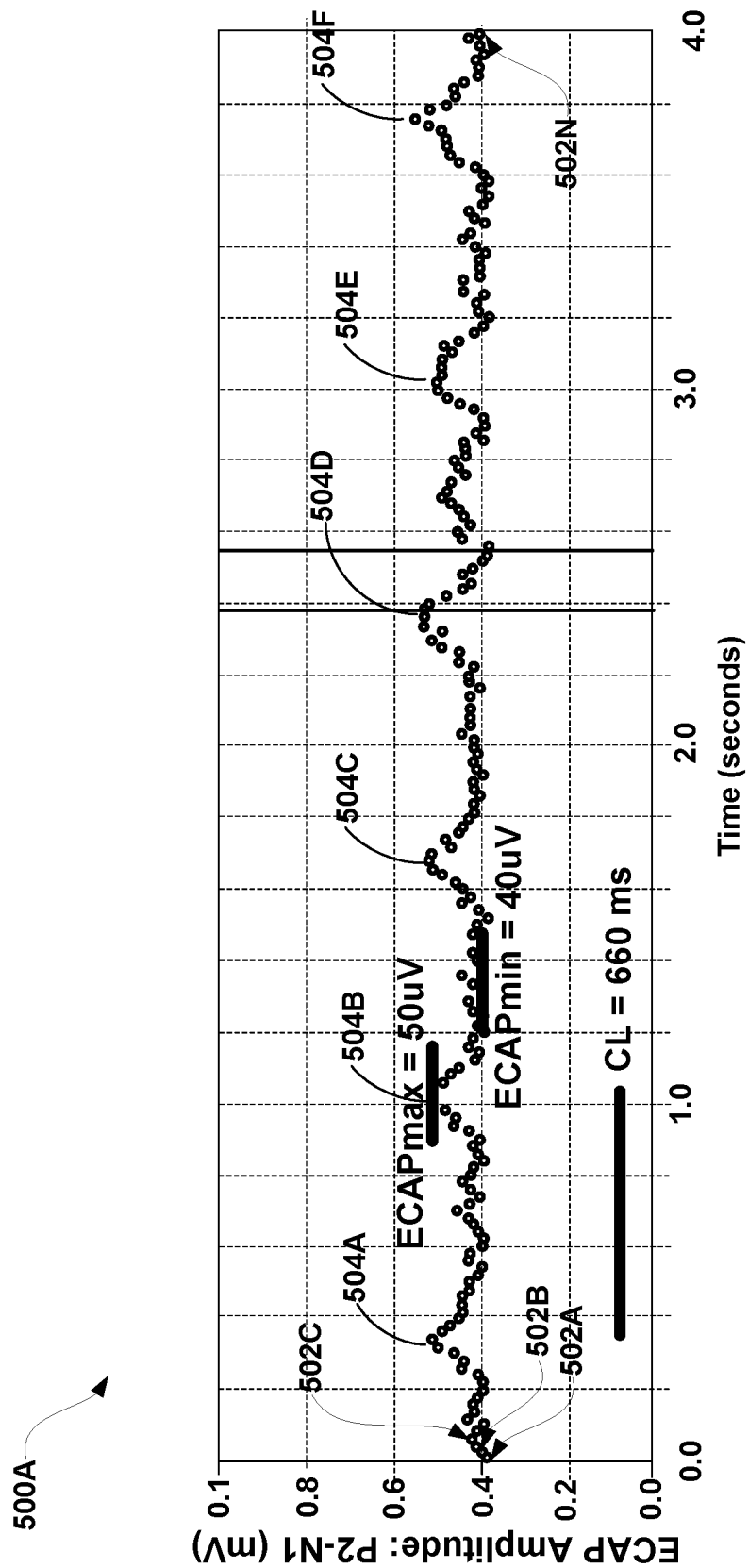
FIGS. 5A and 5B are graphs illustrating example variability in sensed ECAPs due to different types of aggressors, in accordance with one or more techniques of this disclosure.

FIG. 5A is a graph 500A illustrating one example of sensed ECAPs in accordance with one or more techniques of this disclosure. For convenience, FIG. 5A is described with reference to IMD 200 of FIG. 2. As illustrated, graph 500A includes a plurality of sensed ECAPs 502A-502N (collectively "ECAPs 502") that form the curve of data in graph 500A. More specifically, FIG. 5A depicts an example of the effects of a cyclic aggressor on a four-second capture of sensed ECAPs 502.

As a non-limiting, illustrative example, the sensed ECAP signals 502 shown in FIG. 5A may result from a 50 Hertz, balanced biphasic stimulation pulse that may be delivered at about 1100 nano Coulombs per phase (nC/phase) via electrodes 232, 234, and recorded (e.g., sensed) via other electrodes 232, 234 of a percutaneous spinal cord stimulation lead 230.

ECAP values are defined in this example as the voltage difference between the P2 and N1 features of the triphasic ECAP 502 and plotted as a function of time within graph 500A. In other examples, ECAP values may refer to different characteristics of a sensed ECAP signal. As illustrated in FIG. 5A, a cyclic aggressor is causing a repetitive, periodic variation in ECAP values over time. More specifically, the plurality of ECAPs 502 exhibit amplitude variation in the form of an approximately 10 μV pulse 504A-504F (collectively, pulses 504) occurring approximately every half-second (~660 ms), e.g., each pulse increasing the ECAP amplitude from about 40 μV up to about 50 μV, and then back down to about 40 μV again. From this characteristic pattern of sensed ECAP values, it may be ascertained that the patient's heartbeat (of approximately 91 BPM) is acting as a cyclic aggressor, causing the observed variation in ECAP values. For example, each contraction of the ventricles may slightly change the distance between the electrodes and the spinal cord which results in the cyclic change in sensed ECAP values. In some examples, a cyclic aggressor may be present or more present during certain posture states for the patient, and the system may anticipate the type of aggressor being present in response to detecting that the patient is in that posture state.

In some examples in accordance with this disclosure, processing circuitry 208 of IMD 200 (or in other examples, processing circuitry 302 of external programmer 300 of FIG. 3) is configured to analyze the plurality of sensed ECAP signals 502 to identify variation in ECAP amplitudes, and, upon identifying variation, determining if the observed variation corresponds to a known characteristic variation (e.g., an "aggressor signature") corresponding to (e.g., resulting from) either a particular type of aggressor (e.g., for very specific, easily identifiable characteristic variations) or a category of similar types of aggressors (e.g., for more general, less-identifiable variations). For example, processing circuitry 302 may compare the sensed ECAP signals 502 to a set of known characteristic aggressor signatures within aggressor data 218 to attempt to determine an aggressor type or aggressor category causing the observed variability.

Upon identifying one or more aggressor types or aggressor categories, such as an aggressor type or aggressor category that is currently dominating the observed variability in sensed ECAP amplitudes, processing circuitry 208 is configured to determine (e.g., select) an appropriate (e.g., corresponding) set of stimulation-therapy control-policy parameters configured to compensate for the observed variability.

As one illustrative example, for cyclical-type aggressors, such as the heartbeat aggressor dominating the variability shown in graph 500A, processing circuitry 208 may be configured to select (e.g., retrieve) a predetermined set of stimulation control-policy parameters including a relatively lower gain value or an "overdamped" response characteristic, in order to provide for relatively smoother and more-precise control over the volume of neural activation. As one illustrative, non-limiting example, in order to maintain a relatively consistent volume of neural activation with ECAP-servoed closed-loop SCS, processing circuitry 208 may select control-policy parameters including a change in stimulation amplitude (e.g., a gain) of no more than 0.2% with each consecutive stimulation-therapy electrical pulse.

In many cases, cyclical aggressors (such as heartbeat, the digestive cycle, and respiration) may be more apparent (e.g., may appear more distinctly within sensed ECAP signals 502) when the patient is oriented in certain postures (e.g., when the patient is supine, or lying down) compared to other postures (e.g., when the patient is upright). Accordingly, in some examples, processing circuitry 208 is configured to determine the set of control policy parameters in response to determining (e.g., based on received sensor data from sensor 210, such as an accelerometer) that the patient is in a particular posture, such as lying down. The effects of patient posture states on observed ECAP signals are detailed in commonly assigned U.S. patent application Ser. No. 17/100, 455, entitled "CONTROL PULSES AND POSTURE FOR ECAPS" and incorporated by reference herein in its entirety.

Figure 5B:
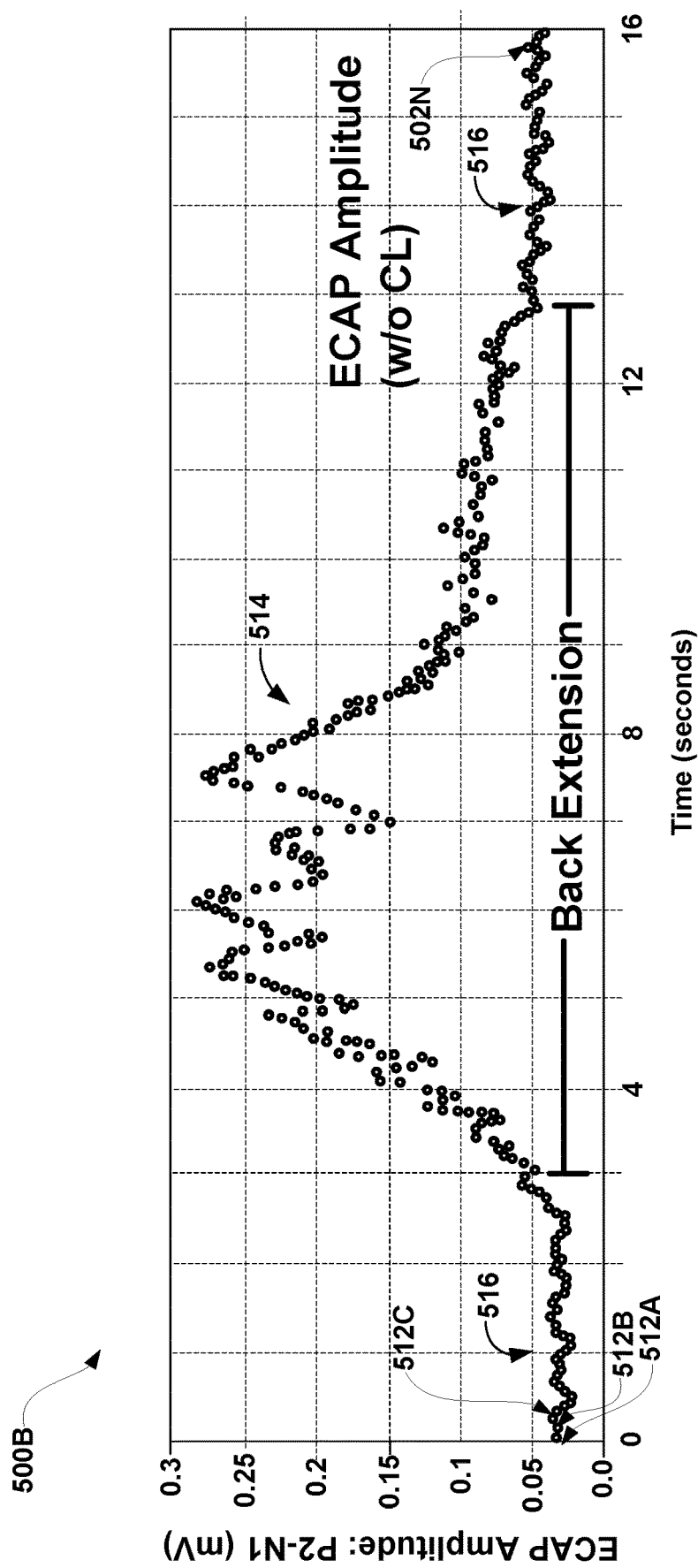

FIG. 5B is a graph 500B illustrating another example of sensed ECAPs in accordance with one or more techniques of this disclosure. For convenience, FIG. 5A is described with reference to IMD 200 of FIG. 2. As illustrated, graph 500B includes a plurality of sensed ECAPs 512A-512N (collectively "ECAPs 512") which collectively result in the shown trace of data in graph 500B. More specifically, FIG. 5B depicts an example of the effects of a transient aggressor on a sixteen-second capture of sensed ECAPs 512.

As a non-limiting, illustrative example, the sensed ECAP signals 512 shown in FIG. 5B may result from a 50 Hertz, balanced biphasic stimulation pulse that may be delivered at about 550 nC/phase via electrodes 232, 234 and recorded (e.g., sensed) via other electrodes 232, 234 of a percutaneous spinal cord stimulation lead 230.

As illustrated in FIG. 5B, a transient (e.g., non-periodic or non-cyclical) aggressor is causing a substantially continuous variation 514 in ECAP amplitudes over time. More specifically, the plurality of ECAPs 512 exhibit an amplitude variation in the form of an approximately 250 μV ECAP change 514, as measured relative to the baseline ECAP amplitude 516 of about 50 μV.

Although the particular transient aggressor resulting in ECAP variation 514 may be the result of a change in patient posture (e.g., from the patient making an arching motion with his back), the particular ECAP signal may not include enough unique characteristics for processing circuitry 208 to determine (e.g., identify) the particular aggressor source. In other words there may be virtually limitless types of patient motions or movements that may result in an ECAP variability that is substantially similar to variability 514 observed in graph 500B. In some such scenarios, either or both of the following responses may apply.

In some examples in which processing circuitry 208 cannot identify a particular aggressor type or aggressor cause, processing circuitry 208 may be configured to select (e.g., retrieve) and apply a set of stimulation-therapy control policy parameters that apply to a wide variety of different types of aggressors, or in other words, a set of parameters for a common category or group of similar types of aggressors (e.g., aggressors having similar effects on ECAP variability). In other examples, processing circuitry 208 may be configured to receive additional input data (e.g., sensor data from sensor 210 or user-input data via UI 306 of FIG. 3) configured to help determine (e.g., identify) a particular aggressor type (or at least narrow down a candidate list of potential aggressor types), such that processing circuitry 208 may select a respective set of control policy parameters that are more-highly tailored to compensate for the observed variability 514. As non-limiting examples of the additional input data, processing circuitry 208 may attempt to determine an aggressor type or category based on any or all of: accelerometer data; the time of day (potentially indicative of a posture of the patient); pulse oximetry data; sensed muscular activity data; cardiac sensor data; respiratory sensor data; gastrointestinal sensor data; sensed analyte data; or manual input data.

Upon identifying one or more aggressor types or aggressor categories, such as an aggressor type or aggressor category that is currently dominating the observed variability in sensed ECAP amplitudes, processing circuitry 208 is configured to determine (e.g., select) an appropriate (e.g., corresponding) set of stimulation-therapy control-policy parameters configured to compensate for the observed variability. As an illustrative example, for transient-type aggressors, such as the back-arch aggressor dominating the variability shown in graph 500B, processing circuitry 208 may be configured to select or retrieve from memory a predetermined set of stimulation control-policy parameters including a relatively higher gain value or an "underdamped" response characteristic, in order to result in a controlled volume of neural activation.

For example, as compared to the ~0.2% gain value employed in the example described with respect to FIG. 5A, to compensate for ECAP variability 514 of FIG. 5B, processing circuitry 208 may select control-policy parameters that include a gain value of about 2.0% with each consecutive stimulation-therapy electrical pulse, approximately ten-times higher. Accordingly, in some examples, detected aggressors associated with higher rates of variability may be configured to trigger a selected set of control policy parameters with relatively higher gain values. While these types of higher-gain control policy parameters may be relatively well-suited for larger ECAP amplitude changes where faster response dynamics are required to compensate, these control characteristics may not be appropriate at other times, for example, for relatively smaller (amplitude) and/or shorter (duration) ECAP variations, such as variations 504 shown in FIG. 5A. Accordingly, the techniques of this disclosure provide the advantage of enabling customized, predefined control policy parameters to more-quickly and more-accurately compensate for different types of unintentional, undesired variations in sensed ECAP values.

Figure 6:
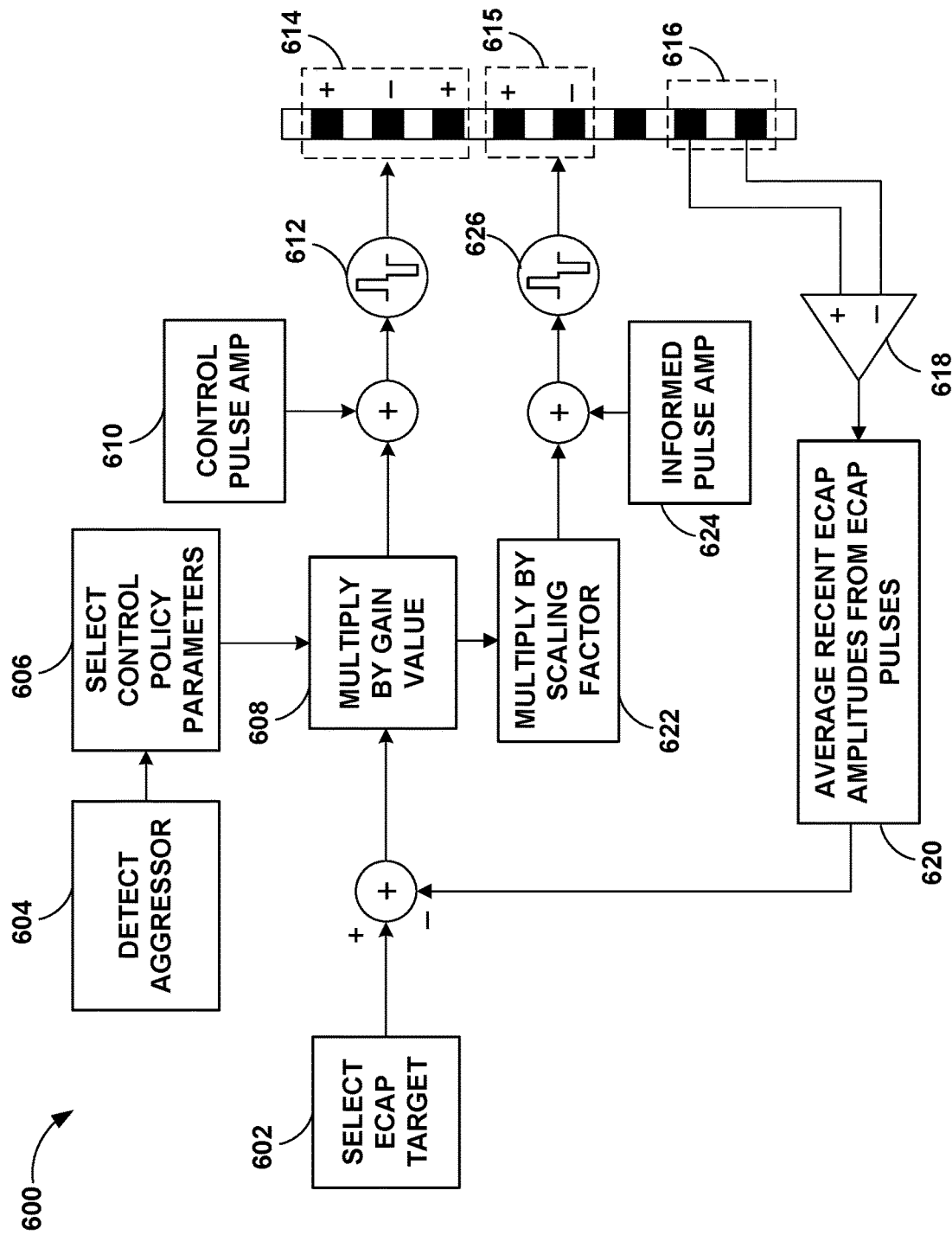
FIG. 6 is a diagram illustrating an example technique for adjusting electrical stimulation therapy based on selected gain values, in accordance with one or more techniques of this disclosure.

FIG. 6 is a diagram illustrating an example technique 600 for adjusting stimulation therapy. As shown in the example of FIG. 6, the system, such as IMD 200 or any other device or system described herein, may dynamically adjust pulse amplitude (or other parameter) based on the gain value representing the patient sensitivity to stimulation. Processing circuitry 208 of IMD 200 may control stimulation generator 204 to deliver a stimulation pulses, such as informed pulses and control pulses, to a patient. Processing circuitry 208 may then control sensing circuity 206 to sense an ECAP signal elicited by the control pulse and then identify a characteristic of the ECAP signal (e.g., an amplitude of the ECAP signal). Processing circuitry 208 may then determine, based on the characteristic of the ECAP signal and a gain value associated with a characteristic ECAP signature, a parameter value (e.g., an amplitude, pulse width value, pulse frequency value, and/or slew rate value) that at least partially defines stimulation pulses, such as control pulses and informed pulses. Processing circuitry 208 may then control stimulation generator 204 to deliver the informed pulses and control pulses according to the determined stimulation parameters.

As shown in FIG. 6, control pulse 612 is delivered to the patient via electrode combination 614, shown as a guarded cathode of three electrodes. The resulting ECAP is sensed by the two electrodes at the opposing end of the lead of electrode combination 616 fed to a differential amplifier 618. For each sensed ECAP, processing circuitry 208 may measure an amplitude of a portion of the ECAP signal, such as the N1-P2 voltage amplitude from the portion of the ECAP signal. Processing circuitry 208 may average the recently measured ECAP amplitudes, such as averaging the most recent, and consecutive, 2, 3, 4, 5, 6, or more ECAP amplitudes. In some examples, the average may be a mean or median value. In some examples, one or more ECAP amplitudes may be ignored from the calculations if the amplitude value is determined to be an error. The measured amplitude (or average measured amplitude) is then subtracted from the selected target ECAP amplitude 602 to generate a differential amplitude. The selected target ECAP amplitude 602 may be determined from an ECAP sensed when the physician or patient initially discovers effective therapy from the informed pulses and/or control pulses. This target ECAP amplitude 602 may essentially represent a reference distance between the stimulation electrodes and the target neurons (e.g., the spinal cord for the case of SCS).

The differential amplitude is then multiplied by the gain value for the patient to generate a differential value 608. Processing circuitry 208 may detect aggressor 604 at varying intervals including, e.g., periodic time intervals, at certain steps of the technique 600, in response to a trigger event, or continuously. For example, processing circuitry 208 may be continuously detecting aggressor(s) 604 in order to select a gain value and/or other control policy parameters 606 that are associated with the detected aggressor. Once the control policy parameters 606 are selected, a gain value can be determined to generate the differential value 608. In other examples, processing circuitry 208 may select the gain value directly from the detected aggressor instead of first selecting the associated control policy parameters. Processing circuitry 208 may add the differential value to the ECAP pulse amplitude to generate the new, or adjusted, control pulse amplitude 810 that at least partially defines the next pulse 812.

The following formulas may represent the function used to calculate the pulse amplitude of the next pulse 612. Equation 1 below represents an equation for calculating the new current amplitude using a linear function, wherein $A_C$ is the current pulse amplitude, D is the differential amplitude (e.g., obtained by subtracting the measured amplitude from the target ECAP amplitude), G is a real number for the gain value, and $A_N$ is the new pulse amplitude:

$$A_N = A_C + (D \times G) \quad (1)$$

In this manner, the gain value G may not change for a given input. Alternatively, processing circuitry 208 may calculate the gain value G such that the gain value varies according to one or more inputs or factors, such as a determined aggressor or aggressor category. In this manner, for a given input or set of inputs, processing circuitry 208 may change the gain value G. Equation 2 below represents an example linear function for calculating the gain value, wherein M is a multiplier, D is the differential amplitude by subtracting the measured amplitude from the target ECAP amplitude, and G is the gain value:

$$G = M \times D \quad (2)$$

Processing circuitry 208 may use the gain value G calculated in Equation 2 in Equation 1. This would result in Equation 1 being a non-linear function for determining the new current amplitude. According to Equation 2 above, the gain value G may be greater for larger differences between the measured amplitude and the target ECAP amplitude. Thus, gain value G will cause non-linear changes to the current amplitude. In this manner, the rate of change in the current amplitude will be higher for larger differences between the measured amplitude and the target ECAP amplitude and lower for smaller differences between the measured amplitude and the target ECAP amplitude. In other examples, a non-linear function may be used to calculate the gain value G.

To adjust the informed pulse amplitude, the differential value 608 is multiplied by a scaling factor 622 to generate the informed differential value. For example, the scaling factor may be the ratio of the previously delivered informed pulse amplitude to the previously delivered control pulse amplitude. The informed differential value is then added to the previously delivered informed pulse amplitude 624 to generate the new, or adjusted, informed pulse amplitude that at least partially defines the next informed pulse 626. The next informed pulse 626 is then delivered, interleaved with control pulse 812, to the patient via electrode combination 615. In some examples, at least two control pulses may be delivered, and at least two respective ECAP signals sensed, between consecutive informed pulses. This increased frequency of nontherapeutic pulses may allow the system to quickly adjust informed pulse amplitudes for any changes in the distance between electrodes and neurons. Although electrode combination 615 is different than electrode combinations 614 and 616, electrode combination 615 can be any set of electrodes on the lead as desired for therapy because the informed pulse is delivered in a non-overlapping fashion with control pulses and sensed ECAP signals.

The pulse width of the informed pulse may be greater than approximately 300 μs and less than approximately 1000 μs. In other examples, the pulse width of the informed pulse may be less than approximately 300 μs or greater than 1000 μs. The stimulation pulse may be a monophasic pulse followed a passive recharge phase. However, in other examples, the pulse may be a bi-phasic pulse that includes a positive phase and a negative phase. In some examples, a pulse may be less than 300 μs, but the following passive recharge phase or even an active recharge phase (of a bi-phasic pulse) may still obscure the detectable ECAP signal from that pulse. In yet another example, the informed pulses may consist of a plurality of pulses at a higher frequency than the control pulse.

In some examples, depending upon, at least in part, the pulse width of the control pulse, IMD 200 may not sufficiently detect an ECAP signal because the stimulation pulse is also detected as an artifact that obscures the ECAP signal. If ECAPs are not adequately recorded, then ECAPs arriving at IMD 200 cannot be used to determine the efficacy of stimulation parameter settings, and electrical stimulation signals cannot be altered according to responsive ECAPs. In some examples, pulse widths of the control pulses may be less than approximately 300 μs, which may increase the number of ECAP signals detected. Similarly, high pulse frequencies may interfere with IMD 110 sufficiently detecting ECAP signals. For example, at pulse frequency values (e.g., greater than 1 kHz) that cause IMD 110 to deliver another control pulse before an ECAP from the previous pulse can be detected, IMD 110 may not be capable to detecting the ECAP.

Figure 7:
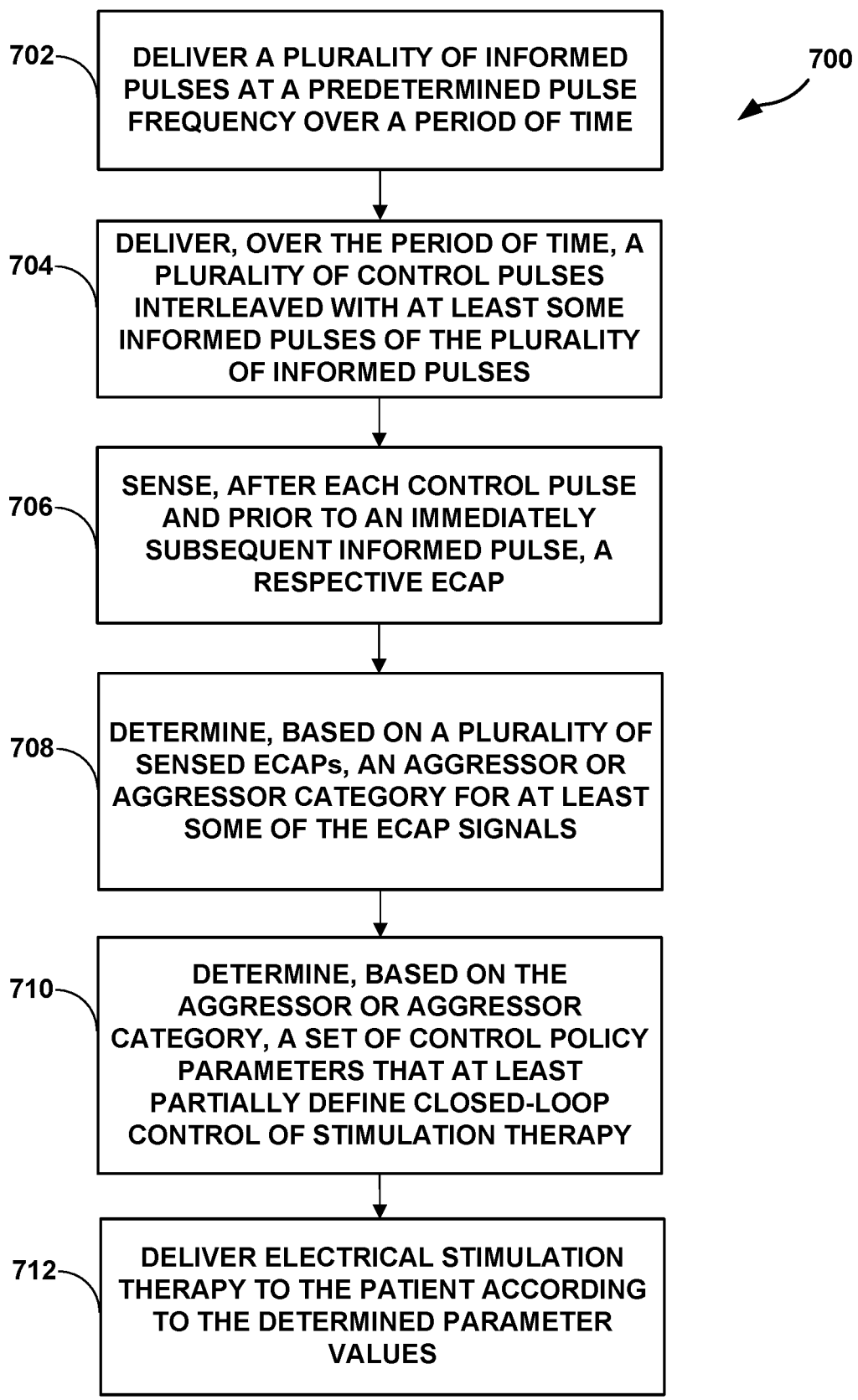
FIG. 7 is a flowchart illustrating an example operation for controlling delivery of electrical stimulation pulses based on determined types of aggressors, in accordance with one or more techniques of this disclosure.

FIG. 7 is a flowchart illustrating an example operation 700 for controlling stimulation therapy, according to techniques of this disclosure. For convenience, FIG. 7 is described with respect to processing circuitry 208 of IMD 200 of FIG. 2. However, the techniques of FIG. 7 may be performed by different components of IMD 200 or by additional or alternative medical devices in some examples.

In the example of FIG. 7, IMD 200 delivers electrical stimulation therapy to patient 102, the electrical stimulation therapy comprising a plurality of informed pulses at a predetermined pulse frequency over a period of time (702). Furthermore, IMD 200 delivers, over the period of time, a plurality of control pulses interleaved with at least some informed pulses of the plurality of informed pulses (704).

For example, one or more control pulses may be delivered between consecutive informed pulses. As another example, one or more informed pulses may be delivered between consecutive control pulses. IMD 200 may sense, after each control pulse and prior to an immediately subsequent informed pulse of the plurality of informed pulses, a respective ECAP (706).

Subsequent to the sensing of a plurality of ECAPs in this way, IMD 200 may determine or identify, based on a characteristic shape or pattern of variability across the values of at least some of the plurality of sensed ECAPs, an aggressor (or category of similar aggressors) associated with the observed variability (708). For example, IMD 200 may compare characteristics of the observed ECAP variability to a set of aggressor signatures stored in memory in order to identify one or more aggressors or aggressor categories dominating the observed variability. In some examples, but not all examples, IMD 200 may also receive additional input data (e.g., sensor data or user input data) to help determine the aggressor or aggressor category resulting in the observed ECAP variability.

Subsequent to determining or identifying an aggressor or aggressor category causing ECAP variability, IMD 200 may determine a respective set of control policy parameters that at least partially define closed-loop control of stimulation therapy, where the control policy parameters are associated with the determined aggressor or aggressor type and tailored to compensate for the observed ECAP variability (e.g., in order to return sensed ECAP amplitude values toward a target ECAP value) (710). In some examples, the control policy parameters may include at least a gain value defining a change in stimulation amplitude between subsequent stimulation pulses. In some examples, IMD 200 may select from two types of aggressors, such as cyclic aggressors or transient aggressors. In other examples, IMD 200 may select from three or more different types of aggressors, all associated with different control policy parameters such as the gain. IMD 200 may use a standard gain value to use during operation and switch to a particular type of aggressor and associated gain value upon detection. In other examples, IMD 200 may determine the control policy parameters directly from the identified ECAP value variability without identifying a type of aggressor associated with the variability. In still other examples, IMD 200 may receive input data, such as accelerometer output, that indicates a posture state typically associated with certain aggressors and select the respective gain value for that posture state in which that certain aggressor is typically present.

As discussed herein, IMD 200 may update determined control policy parameters, continuously or non-continuously, to adjust for different variations of sensed ECAP values. IMD 200 then delivers, via electrodes 108, the electrical stimulation therapy to spinal cord 106 of patient 102 according to the adjusted one or more informed parameter values (712).

The following numbered examples illustrate some techniques of this disclosure.

Example 1: A method includes: receiving, via a sensing electrode located at a target region of a patient, a plurality of evoked compound action potential (ECAP) signals elicited from respective electrical stimuli delivered to the patient; determining, based on the plurality of ECAP signals, an aggressor category for at least some ECAP signals of the plurality of ECAP signals, the aggressor category determined from a plurality of aggressor categories; determining, based on the aggressor category, a set of control policy parameters that at least partially define closed-loop control of stimulation therapy; and controlling delivery of the stimulation therapy according to at least the set of control policy parameters and one or more subsequent ECAP signals.

Example 2: The method of example 1, wherein the target region includes a spinal cord of the patient.

Example 3: The method of example 1 or example 2, wherein the plurality of aggressor categories includes a transient aggressor and a cyclic aggressor.

Example 4: The method of example 3, wherein the aggressor category includes the transient aggressor, and wherein the transient aggressor includes at least one of: an arching of the patient's back; a cough; a motion of the patient's leg; a sneeze; a laugh; a motion of the patient's arm; or a rotation, extension, or flexion of the patient's cervical spine.

Example 5: The method of example 3, wherein the aggressor category includes the cyclic aggressor, and wherein the cyclic aggressor includes at least one of: a heartbeat of the patient; respiration of the patient; or a digestive cycle of the patient.

Example 6: The method of example 3, wherein the aggressor category includes the transient aggressor, and wherein determining the set of control policy parameters includes selecting a set of higher-gain control policy parameters defining a more-underdamped response.

Example 7: The method of example 3, wherein the aggressor category includes the cyclic aggressor, and wherein determining the set of control policy parameters includes selecting a set of lower-gain control policy parameters defining a more-overdamped response.

Example 8: The method of any of examples 1 through 7, wherein the method further includes receiving input data, wherein determining the aggressor category includes determining the aggressor category based on the input data and the plurality of ECAP signals, and wherein the input data includes accelerometer data; a time of day; pulse oximetry data; sensed muscular activity data; cardiac sensor data; respiratory sensor data; gastrointestinal sensor data; sensed analyte data; or manual user input data.

Example 9: The method of example 8, wherein the method further includes determining, based on the input data, that the patient is lying down, and wherein determining the set of control policy parameters that at least partially define the closed-loop control of the stimulation therapy includes selecting the set of control policy parameters in response to determining that the patient is lying down.

Example 10: The method of any of examples 1 through 9, wherein the aggressor category indicates an aggressor source modifying a spacing between the sensing electrode and the target region of the patient.

Example 11: The method of any of examples 1 through 10, wherein the method further includes identifying, within the plurality of ECAP signals, an aggressor signature; wherein determining the aggressor category includes determining the aggressor category based at least in part on the aggressor signature.

Example 12: The method of any of examples 1 through 11, wherein the set of control policy parameters includes a gain value that defines a rate of change for at least one stimulation parameter value of a subsequent pulse of the stimulation therapy, and wherein the aggressor category identifies the gain value.

Example 13: A medical system includes a device configured to: receive, from a sensing electrode located at a target region of a patient, a plurality of evoked compound action potential (ECAP) signals elicited from respective electrical stimuli delivered to the patient; determine, based on the plurality of ECAP signals, an aggressor category for at least some ECAP signals of the plurality of ECAP signals, the aggressor category determined from a plurality of aggressor categories; determine, based on the aggressor category, a set of control policy parameters that at least partially define closed-loop control of stimulation therapy; and control delivery of the stimulation therapy according to at least the set of control policy parameters and one or more subsequent ECAP signals.

Example 14: The medical system of example 13, wherein the device further includes sensing circuitry that includes the sensing electrode.

Example 15: The medical system of example 13 or example 14, wherein the system further includes stimulation circuitry configured to provide the stimulation therapy to the patient.

Example 16: The medical system of any of examples 13 through 15, wherein the aggressor category includes a transient aggressor, and wherein the transient aggressor includes at least one of: an arching of the patient's back; a cough; a motion of the patient's leg; a sneeze; a laugh; a motion of the patient's arm; or a rotation, extension, or flexion of the patient's cervical spine.

Example 17: The medical system of any of examples 13 through 16, wherein the aggressor category includes a transient aggressor, and wherein determining the set of control policy parameters includes selecting a set of higher-gain control policy parameters defining a more-underdamped response.

Example 18: The medical system of any of examples 13 through 17, wherein the aggressor category includes a cyclic aggressor, and wherein the cyclic aggressor includes at least one of: a heartbeat of the patient; respiration of the patient; or a digestive cycle of the patient.

Example 19: The medical system of any of examples 13 through 18, wherein the aggressor category includes a cyclic aggressor, and wherein determining the set of control policy parameters includes selecting a set of lower-gain control policy parameters defining a more-overdamped response.

Example 20: The medical system of any of examples 13 through 19, wherein the set of control policy parameters includes a gain value that defines a rate of change for at least one stimulation parameter value of a subsequent pulse of the stimulation therapy, and wherein the aggressor category identifies the gain value.

Example 21: The medical system of any of examples 13 through 20, wherein the device is further configured to receive input data, wherein the device is configured to determine the aggressor category based on the input data and the plurality of ECAP signals, and wherein the input data includes: accelerometer data; a time of day; pulse oximetry data; sensed muscular activity data; cardiac sensor data; respiratory sensor data; gastrointestinal sensor data; sensed analyte data; or manual user input data.

Example 22: The medical system of example 21, wherein the device is further configured to determine, based on the input data, that the patient is lying down, and wherein the device is configured to determine the set of control policy parameters that at least partially define the closed-loop control of the stimulation therapy by selecting the set of control policy parameters in response to determining that the patient is lying down.

Example 23: A non-transitory, computer-readable medium includes instructions that, when executed by a processor, cause the processor to: receive, from a sensing electrode located at a target region of a patient, a plurality of evoked compound action potential (ECAP) signals elicited from respective electrical stimuli delivered to the patient; determine, based on the plurality of ECAP signals, an aggressor category for at least some ECAP signals of the plurality of ECAP signals, the aggressor category determined from a plurality of aggressor categories; determine, based on the aggressor category, a set of control policy parameters that at least partially define closed-loop control of stimulation therapy; and control delivery of the stimulation therapy according to at least the set of control policy parameters and one or more subsequent ECAP signals.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:
1. A method comprising:
  receiving, via a sensing electrode located at a target region of a patient, a plurality of evoked compound action potential (ECAP) signals elicited from respective electrical stimuli delivered to the patient during stimulation therapy;
  determining, based on the plurality of ECAP signals, an aggressor category for at least some ECAP signals of the plurality of ECAP signals, the aggressor category determined from a plurality of aggressor categories;
  determining, based on the aggressor category, a set of control policy parameters that at least partially define closed-loop control adjustment to one or more parameters that define the stimulation therapy; and controlling delivery of the stimulation therapy according to at least the set of control policy parameters and one or more subsequent ECAP signals.

2. The method of claim 1, wherein the target region comprises a spinal cord of the patient.

3. The method of claim 1, wherein the plurality of aggressor categories comprises a transient aggressor and a cyclic aggressor.

4. The method of claim 3, wherein the aggressor category comprises the transient aggressor, and wherein the transient aggressor comprises at least one of:
an arching of the patient's back;
a cough;
a motion of the patient's leg;
a sneeze;
a laugh;
a motion of the patient's arm; or
a rotation, extension, or flexion of the patient's cervical spine.

5. The method of claim 3, wherein the aggressor category comprises the cyclic aggressor, and wherein the cyclic aggressor comprises at least one of:
a heartbeat of the patient;
respiration of the patient; or
a digestive cycle of the patient.

6. The method of claim 3, wherein the aggressor category comprises the transient aggressor, and wherein determining the set of control policy parameters comprises selecting a set of higher-gain control policy parameters defining a more-underdamped response.

7. The method of claim 3, wherein the aggressor category comprises the cyclic aggressor, and wherein determining the set of control policy parameters comprises selecting a set of lower-gain control policy parameters defining a more-overdamped response.

8. The method of claim 1, further comprising receiving input data, wherein determining the aggressor category comprises determining the aggressor category based on the input data and the plurality of ECAP signals, and wherein the input data comprises:
accelerometer data;
a time of day;
pulse oximetry data;
sensed muscular activity data;
cardiac sensor data;
respiratory sensor data;
gastrointestinal sensor data;
sensed analyte data; or
manual user input data.

9. The method of claim 8, further comprising determining, based on the input data, that the patient is lying down, wherein determining the set of control policy parameters that at least partially define the closed-loop control adjustment to one or more parameters that define the stimulation therapy comprises selecting the set of control policy parameters in response to determining that the patient is lying down.

10. The method of claim 1, wherein the aggressor category indicates an aggressor source modifying a spacing between the sensing electrode and the target region of the patient.

11. The method of claim 1, further comprising identifying, within the plurality of ECAP signals, an aggressor signature; wherein determining the aggressor category comprises determining the aggressor category based at least in part on the aggressor signature.

12. The method of claim 1, wherein the set of control policy parameters comprises a gain value that defines a rate of change for at least one stimulation parameter value of a subsequent pulse of the stimulation therapy, and wherein the aggressor category identifies the gain value.

13. A medical system comprising a device configured to:
receive, from a sensing electrode located at a target region of a patient, a plurality of evoked compound action potential (ECAP) signals elicited from respective electrical stimuli delivered to the patient during stimulation therapy;
determine, based on the plurality of ECAP signals, an aggressor category for at least some ECAP signals of the plurality of ECAP signals, the aggressor category determined from a plurality of aggressor categories;
determine, based on the aggressor category, a set of control policy parameters that at least partially define closed-loop control adjustment to one or more parameters that define the stimulation therapy; and
control delivery of the stimulation therapy according to at least the set of control policy parameters and one or more subsequent ECAP signals.

14. The medical system of claim 13, wherein the device further comprises sensing circuitry that comprises the sensing electrode.

15. The medical system of claim 13, further comprising stimulation circuitry configured to provide the stimulation therapy to the patient.

16. The medical system of claim 13, wherein the aggressor category comprises a transient aggressor, and wherein the transient aggressor comprises at least one of:
an arching of the patient's back;
a cough;
a motion of the patient's leg;
a sneeze;
a laugh;
a motion of the patient's arm; or
a rotation, extension, or flexion of the patient's cervical spine.

17. The medical system of claim 13, wherein the aggressor category comprises a transient aggressor, and wherein determining the set of control policy parameters comprises selecting a set of higher-gain control policy parameters defining a more-underdamped response.

18. The medical system of claim 13, wherein the aggressor category comprises a cyclic aggressor, and wherein the cyclic aggressor comprises at least one of:
a heartbeat of the patient;
respiration of the patient; or
a digestive cycle of the patient.

19. The medical system of claim 13, wherein the aggressor category comprises a cyclic aggressor, and wherein determining the set of control policy parameters comprises selecting a set of lower-gain control policy parameters defining a more-overdamped response.

20. The medical system of claim 13, wherein the set of control policy parameters comprises a gain value that defines a rate of change for at least one stimulation parameter value of a subsequent pulse of the stimulation therapy, and wherein the aggressor category identifies the gain value.

21. The medical system of claim 13, wherein the device is further configured to receive input data, wherein the device is configured to determine the aggressor category based on the input data and the plurality of ECAP signals, and wherein the input data comprises:
- accelerometer data;
- a time of day;
- pulse oximetry data;
- sensed muscular activity data;
- cardiac sensor data;
- respiratory sensor data;
- gastrointestinal sensor data;
- sensed analyte data; or
- manual user input data.

22. The medical system of claim 21, wherein the device is further configured to determine, based on the input data, that the patient is lying down, and wherein the device is configured to determine the set of control policy parameters that at least partially define the closed-loop control adjustment to one or more parameters that define the stimulation therapy by selecting the set of control policy parameters in response to determining that the patient is lying down.

23. A non-transitory, computer-readable medium comprising instructions that, when executed by a processor, cause the processor to:
- receive, from a sensing electrode located at a target region of a patient, a plurality of evoked compound action potential (ECAP) signals elicited from respective electrical stimuli delivered to the patient during stimulation therapy;
- determine, based on the plurality of ECAP signals, an aggressor category for at least some ECAP signals of the plurality of ECAP signals, the aggressor category determined from a plurality of aggressor categories;
- determine, based on the aggressor category, a set of control policy parameters that at least partially define closed-loop control adjustment to one or more parameters that define the stimulation therapy; and
- control delivery of the stimulation therapy according to at least the set of control policy parameters and one or more subsequent ECAP signals.

* * * * *